United States Patent
Waldor et al.

(10) Patent No.: US 7,247,437 B2
(45) Date of Patent: Jul. 24, 2007

(54) VIBRIONACEAE REPLICATION FACTORS AND METHODS OF USE THEREOF

(75) Inventors: Matthew K. Waldor, Newton, MA (US); Elizabeth S. Egan, Jamaica Plain, MA (US)

(73) Assignee: Trustees of Tufts College, Boston, MA (US)

( * ) Notice: Subject to any disclaimer, the term of this patent is extended or adjusted under 35 U.S.C. 154(b) by 205 days.

(21) Appl. No.: 10/922,792

(22) Filed: Aug. 20, 2004

(65) Prior Publication Data

US 2005/0130921 A1 Jun. 16, 2005

Related U.S. Application Data

(60) Provisional application No. 60/496,791, filed on Aug. 21, 2003.

(51) Int. Cl.
*C12Q 1/68* (2006.01)
(52) U.S. Cl. .......................................................... 435/6
(58) Field of Classification Search ...................... 435/6
See application file for complete search history.

(56) References Cited

OTHER PUBLICATIONS

Myhr et al. 1991; Applied and Environmental Microbiology 57(9): 2750-2757.*
Paulo et al. 1994; J. Ethnopharmacology 44: 127-130.*
Dixon et al. 1995; J. Aquatic Animal Health 7:42-45.*
Kim et al. 1995; J. Agric Food Chem. 43: 2839-2845.*
Al-Dagal et al. 2001; Fishery Technology 38(1): 36-42.*
Ho et al. 2002; Fish Pathology 37(1): 7-12.*
Chhotray et al. 2002; Epidemiol. Infect. 128:131-138.*
Abeles et al., J. Bacteriol. 175: 7801-7807, 1993.
Boye et al., Cell 62: 981-989, 1990.
Boye et al., EMBO Rep. 1: 479-483, 2000.
Bramhill et al. Cell 52: 743-755, 1988.
Cabezon et al., Mol. Gen. Genet. 254: 400-406, 1997.
Campbell et al., Cell 62: 967-979, 1990.
Chattoraj, Mol. Microbiol. 37: 467-476, 2000.
del Solar et al., Microbiol. Mol. Biol. Rev. 62: 434-464, 1998.
DelVecchio et al., Proc. Natl. Acad. Sci. USA 99: 443-448, 2002.
Egan et al., Cell 114: 521-530, 2003.
Fuller et al., Cell 38: 889-900, 1984.
Guo et al., Nucleic Acids Res. 31: 1780-1789, 2003.
Hansen et al., Proc. Natl. Acad. Sci. USA 83: 4423-4427, 1986.
Heidelberg et al., Nature 406: 477-483, 2000.
Jensen et al., J. Mol. Biol. 215: 257-265, 1990.
Julio et al., Infect. Immun. 69: 7610-7615, 2001.
Katayama et al., Cell 94: 61-71, 1998.
Kitagawa et al., Mol. Microbiol. 19: 1137-1147, 1996.
Kita-Tsukamoto et al., Int. J. Syst. Bacteriol. 43: 8-19, 1993.
Kurokawa et al., EMBO J. 18: 6642-6652, 1999.
Lessl et al., J. Bacteriol. 174: 2493-2500, 1992.
Lobner-Olesen et al., EMBO J. 15: 5999-6008, 1996.
Lobner-Olesen et al., Mol. Microbiol. 6: 1841-1851, 1992.
Lu et al., Cell 77: 413-426, 1994.
Marinus, Methylation of DNA. In: Neidhardt, F.C., Editor, 1996. *Escherichia coli* and *Salmonella*, ASM Press, Washington, D.C. 697-702, 1996.
Marszalek et al., J. Biol. Chem. 269: 4883-4890, 1994.
Messer et al., Initiation of chromosome replication, In: Neidhardt, F.C., Editor, 1996. *Escherichia coli* and *Salmonella*, ASM Press, Washinton, D.C. 1579-1601, 1996.
Miller et al, J. Bacteriol. 170: 2575-2583, 1988.
Moyer et al., Mol. Microbiol. 41: 311-323, 2001.
Novick, Microbiol. Rev. 51: 381-395, 1987.
Papp et al., J. Biol. Chem. 269: 23563-23568, 1994.
Pearson et al., Proc. Natl. Acad. Sci. USA 90: 3750-3754, 1993.
Russell et al., Cell 50: 1071-1079, 1987.
Slominska et al., Mol. Microbiol. 40: 1371-1379, 2001.
Trucksis et al., Proc. Natl. Acad. Sci. USA 95: 14464-14469, 1998.
Weitao et al., EMBO Rep. 1: 494-499, 2000.
Yamaichi et al., Mol. Microbiol. 31: 1513-1521, 1999.
Zyskind et al., Proc. Natl. Acad. Sci. USA 80: 1164-1168, 1983.

* cited by examiner

*Primary Examiner*—Karen Cochrane Carlson
(74) *Attorney, Agent, or Firm*—Lawson & Weitzen, LLP; Sonia K. Guterman; Adam M. Schoen

(57) ABSTRACT

The invention relates to compositions, methods and kits useful in modulating bacterial cell DNA replication and for treating pathogenic bacterial.

6 Claims, 10 Drawing Sheets

| | | | | | |
|---|---|---|---|---|---|
V.cholerae       CACTCAGGT TGTGGATAA ACTGTGTGAGCAC C TTGATCATGCTT AGAAGCTTACG TTGATCATTGAT T
V.vulnificus     TCTCACCG C TGTGGATAA GTTGTTTACTCATC ATGATCATGCTT TCCTTCTTACG TTGATCACGCTT G
V.harveyi        GCTAGGAT C TGTGGATAA GTTGTACAAACATC ATGATCATCGTT TCAAGGCTGTT TTGATCATCTTT T
V.parahaemolyticus ACGGATTT C TGTGGATAA CCTGTACAGACATC ATGATCATCGTT TCATGATTGTT TTGATCATCTTT T
V.fischeri       TAGAAATT C TGTGGATAA CTTGTGTTTAGACC ATGATCATTCT T CAATAAAACTC ATGATCATCGAT T
                                                              ├── 11 bp ──┤

CTGTTGACTG ATGATCATGCTT AGAGGAACAA ATGATCATGCTT TCGATCTTGTA TTGATCATGGTT TCCAT
CGCATTCATG ATGATCATCTTT ACGTCTCGGT TTGATCATGTTT TCGCAGTCTAT ATGATCATGCTT TCTGG
CAGAAACTTA ATGATCATGCTT ACGACGTTTT GTGATCATGCTT TCCGGCTCATG TTGATCATCGTT TCGAT
CAGGAACTTA ATGATCATGCTT GCGGAATGAA GTGATCATGCTT TCAAGGTTTTG TTGATCATCGTT TCGGT
CAAATGGACG ATGATCATGCTT TTGAGATTTA ATGATCATTGAT CCAGAGTCATA ATGATCATGCTT TC---
├── 11 bp ──┤       ├── 10 bp ──┤      ├── 11 bp ──┤

CGATAC ATGATCATGCTT CTGAAT-GGCTTAAAATAATCTCTTTTAATTACAATAAATTAGA--ACTAAAAA
ATTATT ATGATCATGCTT CCTAGA-TGGTAAAAATAAACCTTTTGTTTTACAGTAAGTT-----ACTAGCAA
ATAATC ATGATCATAGTT CCGTTAATGAACTTTTAAATATCATTATAAAACAAAAACTTACAGAGCTAAAAA
AAAGCT ATGATCATAGTT CCGAAACACCTCAAAAAAATACTATTTAATAACAGTCGCTTAGGTTCGTAAAAA
------ATGCGTTTATTTTTTTAA---------------TTCTTTATTTTCAGTTACTTAAA-AGCAAAAAA
11 bp ──┤

T--CGTCAC-AGATCATTAGATCACTCTAATCATATTTAATCATT-TAAATCAGAAA GATCAGTTATTTA AA
TTCCGCCGCTAGATCAATAGATCA-TATAATCAATTAAGATCAGA-TTAATCAAAAA GATCAGTTATTTA AA
T-----CTCCAGATCATTAGATCA-TATAATCAATTAAGATCAGA-ATAATCAGAAA GATCAGTTATTTA AA
T-----AACCAGATCAATAGATCA-TATAATCAATTAAGATCAGA-ATAATCAAAAA GATCAGTTATTTA AA
C----CAACCAGATCA-TAGATCAATATAATCATATA-GATCAGAATTAATCATAAA GATCAGTT-TAAA AG

AACA-ACAAATTTTTCTTTATTTAT- GATCTCTTTTTCT TTATTCTCT-TGGAACTATAGTGATATTACGG
AACA-AGCT-TTTTTCTTTATTTAT- GATCTATTTTTCT TTATCCTCT-TGGAACTATAGCGCTTTTACGG
AACCCAAGATTTTTCTTTATTTAT- GATCTGTTTTTCT TTATCCT-T-CGGAACCATAGCAAAACTACGG
AAAC-AAGATTTTTCTTTATTTAT- GATCTGTTTTTCT TTATTCT-T-CGGAACCATAGCACAACTACGG
AATAATAATTTTTTCTTTCTTTAAA GATC-CATTTCCA TTAACCTATACGAAAGAATGATTAAAATACAA

Fig. 7

```
                    |         |         |         |         |
V.cholerae        TAGGTATCACCGAAACG ATGATCAAGAG CAGCAGCTTGATCATTCTTCCGTAAAAAATAG
V.vulnificus      TTTATGTCTCTGGAAGA ATGATCAAGTG ATGCT--TTAATCATTCTTCCTGATA-ATGAG
V.harveyi         TGAAATGAAGCGGAAGT ATGATCAAG-G GGAGTTCTTGATCATACTTCCGGTACTCACAC
V.parahaemolyticus GAATAAGAA-CGGAACC ATGATCAAG-G AAGACTCTTGATCATGTTTTCGAAGATAACTG
V.fischeri        CTTAAAAATTTCGATGT AATAT-AAGAG ATATA-CTTGGGTCTATTTCCATCTT-ATCTG

|         |         |         |         |         |
AGGGTTAAGGAAAC ATGATCAAGAG --CTCATCATGGCTATGAGTCGAGGCAAGAGAATTAACAATTGAA
CCGTTATCGAAACG ATGATCATGGG AATTCATACTGTAAAATAGGCCTTCCGATGATGGCGTT-AATGAT
CAAAA-TCGAAAGC ATGATCAAGGA AATCAACGCATCATTTACATTGCAGCTCGTTTTTTCAA-ACGGAT
TAAAT-ACGAAAGC ATGATCATGGC AGATAATGGACGAATGAAGGTAAATCAAGGCTTGAGTACATGGAT
AGTAAAATAGAAGC ATGATCAAGGG GTATATTCCACAAATAAACAGGTGTAAA---TTGATAAAATGTAA

|         |         |         |         |         |
GATCTTCAATCGGATCG ATGATCAAGAG GTAAATCGTC GCGGAAGCATGTAA ATTCATTATCAA-TTTAC
CCTTATAATACGGAAAG ATGATCAAGT- AGCGATGGAT TCGGAAGCATG-AA AAAATATCACTAAGTTAC
CAATTTA--CCGAAAA  ATGATCAAGTG AATTAACCAC TCGGAAGCATG-TA ATTCTCAAGCTAATTTAC
CCATTTC--TCGAAAA  ATGATCAAGCA AGTAGGTTTC TCGGAAGCATGCTT TTTAATGCGCTA-TTTAC
GTTCTCAGCTAAGAAGC ATGATCAAGCA ATAAATAGCT TCGGAAGCATG-TA TCTTTCTTTCTAAATTAC

|         |         |         |         |         |
GGTCGATGTCAGGCAGAGTAAGGCTTTGGCTAGTCAGT--GATGAAAAACCGTCTATCCTAACAAGTCTC
GGTCAAATGCAGATAGAACGGGAGATCAAGCTCGTTTGGCTCAATTCATCATCTAGTGAGATTGGCTTTC
GGAAGAATGCAGACAGACTGGGGGATAGAGGCAAAAA--CGAATATAAAATCACGGAACGATGAAAACAA
GGCTGAGTGCAGACGGAATGGGGGATTGACGCATAAATGCGCCTCTCAACCTTCGGAACGATGAAAT-AC
AGAGGATGTATATCTGATAAGGCTTCAGA----------GAAGATCAACGAAAAAATCAAATAATT--C

|         |         |         |         |         |
AGTCAAAACAAGATAAACAGAACAACAGCC ATGATCATGCTT TCGT--AATCCC----GCTCCGTCACCT
AG--ATTAGAATATTGACCTTGATA-TGCC GTGATCATGCTT TCGT---ATTTTCTCAATGAAATAGCGA
AGCGAATGCAAAATGTAGAAACTCA-TCTG ATGATCATGCTT CCGTTTAATTAACGCTAATCATTAA---
AGTATCGGCAAACAAGACATAGTGTCTTTC ATGATCATGCTT CCGTT-AATTCT-GATAATCATGCAATC
ACTCAGGTTGATCTAAGAAGAATGG--TAC TTGATCATTCTT CTGAAATACGATTAAAACGCATTAGACT

|         |         |         |         |         |
TGGCCAGCGCAA----TATGGCGCTGAAGATGT--CAATTGGAAGCACAAGTCA-CAAGTAATTGGAAGC
TGAAAGACAAGAAGATAGATTTGCTGATTGTTTAGCCAAACTCAGCGAGAATTGCGGAAACAAACTCAGC
TAAGAGGCACAACCAGCAAAGTAGAGTAAGTTT--TCATCACATGCGCAAATAATATCCACATCACATGC
TTGGAGGC-CAAGGACCAAAATTGACGTCATTT--TAATCGTTTGGCTAATTTGGCAACAAATCGTTTGG
TAAGATCATCTT-----AATTTTATAGCTATTAATGAATTAAAAACGTATTTTC-GGACTAATTAAAAAC

|         |         |         |         |         |
ACAAGTCA-CAAGTATTCATTGCGATATGGCCAAGAAATCATCCT CTCTTGATCAT CTTTCCGTGGTCAT
GAGAATTGCGGAAAAAACATTCG--CATCCTGACAAACAAGCTTT ATGATGATCAT GCTTCCGTCTG---
GCAAATAATATCCAACTCAATGA-ACAGAACGATAAAAAACCTCT CTYTTGATCAT CGATGAGCCGAGTG
CTAATTTGGCAACAATTGAAGGT-AAAGAGAGATGAAATAACCTT AGCTTGATCAT TGATCCACAACCTC
GTATTTC-GGACTAATCTTTGG---TCTTAAATGTCATCCATCA ATAAAAGACAC CTCTCAAAAGGGA
```

Fig. 8

SEQUENCE LISTING

<160> NUMBER OF SEQ ID NOS: 13

<210> SEQ ID NO 1
<211> LENGTH: 1977
<212> TYPE: DNA
<213> ORGANISM: Vibrio cholerae
<220> FEATURE:
<221> NAME/KEY: CDS
<222> LOCATION: (1134)..(3110)

-continued

```
<400> SEQUENCE: 1
atgagctcag aagaaaaacg attgatcaaa ttgccaagaa ctcacaaaga tggtcatctt    60
tttgaagtct ctgaagccgc gattgactgg attgaacagt atcaacactt taaaggtgtc   120
acgaaaagca ttgttgaact tttgaatctg atctcactgc gtggattacg cagtagagat   180
ggcttagttt caaccacaga actgattgat gcaaccgatg ggcagctgac gcgtgcagcc   240
atccagcagc gcttgagagc agcggtagct gttggattgt tcaaacaaat cccagtgcgt   300
tttgaagagg ggctggctgg caaaaccatg ctccatcgtt tcattaaccc caaccaattg   360
atctcggtac tcggctcaac cagcttagtc actgaatcgg ttaagcaaaa tgaaaagcaa   420
aagcgctcaa aagcattagc gcagacgcaa gtcaatcaac gtttactgca tgagcatggt   480
ttaaatacac cgccagccat gaaagatgag gctgatcagt ttgtggtctc accgactaac   540
tgggcaggga tcattgatca agcgttagcg ccacccagaa cccgcaagag ctaccaaaag   600
tctatggttt cgatatcggg tactcgtgct gtgattgaaa cacgatcgtc taaaaacatc   660
atgacggtcg acgatctgat gactttgttt gccttattca ctttaacagt gcaataccat   720
gatcatcacc aagatgatta ccatttcaat gctaaacaag caccaaacaa aacgccgctg   780
tatatcaccg acattctctc tttacgtggc aaaaaagaca cgcgcccggc acgtgactcg   840
atccgtgaca gtattgatcg tattgaattt accgattttc agttgcatga actgacgggt   900
cgttggctca gtgagaatat gccagaaggc tttaaaagcg atcgttttcg ctttttagcg   960
cgcaccatca ccgcttccga agaggcacct gtggaaggca gtgatggcga gatccgcatc  1020
aaacccaatc tgtacatttt ggtgtgggag ccttcgtttt ttgaagagct attgacgcga  1080
gattatttct tcctatttcc accggagatc ttgaaacaac ataccttggt atttcagctc  1140
tactcctatt tccgtagccg aatgtctcgt cgtcataccg atgtaatgat gctgagtgaa  1200
ctcaaccaaa aattggccag aaacatcgaa tggcgacggt tttctatgga tctgatccgc  1260
gaacttcgtc gtctctccga agggaagggg agtgaagatc tgtttgtggt caatctctgg  1320
ggttatcact tgactgtgaa aagcattgaa gagaaaggca aagtggtgga ttaccaagtc  1380
gatatcaaat gtgatgtgga agaggtactg cgctattcac gcgccaaaac caccaacgcg  1440
ggtaaacgca atatggctcc aaccttgcct aacccttta gtaacgagct ggtttccaag  1500
cagaaactgg ctgagttatc gagcatcatc gatggtgaat ttgaaccaat ccagcgcaaa  1560 gcccttcgc cgagaggccg cttaggtcgg cgcgtgaagc tacgtaaaca tcttgtcgaa  1620
atcaatgctg atgaaatcac cattactcta tcgcgttata cctctccaga agcgctagaa  1680
cgcagtataa cggctttagc ggctatgact ggacacgccc cttcatcaat caaagaagag  1740
tgtgtagagc tcatagacaa gctagattgg ctgcgtgttg aaaacgatgt gatccaatac  1800
ccgacattga gcaagctgct tgagctctac aacagccaaa atgagagtaa acatctgtcg  1860
atcgaaaaat tgatcgcagg tttagcggta cgccgtaaag tctgtaaatt ggttcaagat  1920
gggcacattg acgaaacggt gtatcgagcc ttagatgaga tggccgctgg agcctaa    1977
```

<210> SEQ ID NO 2
<211> LENGTH: 658
<212> TYPE: PRT
<213> ORGANISM: Vibrio cholerae

<400> SEQUENCE: 2

```
Met Ser Ser Glu Glu Lys Arg Leu Ile Lys Leu Pro Arg Thr His Lys
1               5                   10                  15
Asp Gly His Leu Phe Glu Val Ser Ala Ala Ile Asp Trp Ile Glu
            20                  25                  30
Gln Tyr Gln His Phe Lys Gly Val Thr Lys Ser Ile Val Glu Leu Leu
            35                  40                  45
Asn Leu Ile Ser Leu Arg Gly Leu Arg Ser Arg Asp Gly Leu Val Ser
    50                  55                  60
Thr Thr Glu Leu Ile Asp Ala Thr Asp Gly Gln Leu Thr Arg Ala Ala
65                  70                  75                  80
Ile Gln Gln Arg Leu Arg Ala Ala Val Ala Val Gly Leu Phe Lys Gln
                85                  90                  95
Ile Pro Val Arg Phe Glu Glu Gly Leu Ala Gly Lys Thr Met Leu His
                100                 105                 110
Arg Phe Ile Asn Pro Asn Gln Leu Ile Ser Val Leu Gly Ser Thr Ser
            115                 120                 125
Leu Val Thr Glu Ser Val Lys Gln Asn Glu Lys Gln Lys Arg Ser Lys
    130                 135                 140
Ala Leu Ala Gln Thr Gln Val Asn Gln Arg Leu Leu His Glu His Gly
145                 150                 155                 160
Leu Asn Thr Pro Pro Ala Met Lys Asp Glu Ala Asp Gln Phe Val Val
                165                 170                 175
Ser Pro Thr Asn Trp Ala Gly Ile Ile Asp Gln Ala Leu Ala Pro Pro
            180                 185                 190
Arg Thr Arg Lys Ser Tyr Gln Lys Ser Met Val Ser Ile Ser Gly Thr
            195                 200                 205
Arg Ala Val Ile Glu Thr Arg Ser Ser Lys Asn Ile Met Thr Val Asp
    210                 215                 220
Asp Leu Met Thr Leu Phe Ala Leu Phe Thr Leu Thr Val Gln Tyr His
225                 230                 235                 240
Asp His His Gln Asp Asp Tyr His Phe Asn Ala Lys Gln Ala Pro Asn
                245                 250                 255
Lys Thr Pro Leu Tyr Ile Thr Asp Ile Leu Ser Leu Arg Gly Lys Lys
            260                 265                 270
Asp Ser Gly Pro Ala Arg Asp Ser Ile Arg Asp Ser Ile Asp Arg Ile
            275                 280                 285
Glu Phe Thr Asp Phe Gln Leu His Glu Leu Thr Gly Arg Trp Leu Ser
    290                 295                 300
Glu Asn Met Pro Glu Gly Phe Lys Ser Asp Arg Phe Arg Phe Leu Ala
305                 310                 315                 320
Arg Thr Ile Thr Ala Ser Glu Glu Ala Pro Val Glu Gly Ser Asp Gly
                325                 330                 335
Glu Ile Arg Ile Lys Pro Asn Leu Tyr Ile Leu Val Trp Glu Pro Ser
            340                 345                 350
Phe Phe Glu Glu Leu Leu Thr Arg Asp Tyr Phe Phe Leu Phe Pro Pro
            355                 360                 365
Glu Ile Leu Lys Gln His Thr Leu Val Phe Gln Leu Tyr Ser Tyr Phe
    370                 375                 380
Arg Ser Arg Met Ser Arg Arg His Thr Asp Val Met Met Leu Ser Glu
385                 390                 395                 400
Leu Asn Gln Lys Leu Ala Arg Asn Ile Glu Trp Arg Arg Phe Ser Met
                405                 410                 415
```

```
Asp Leu Ile Arg Glu Leu Arg Arg Leu Ser Glu Gly Lys Gly Ser Glu
            420                 425                 430

Asp Leu Phe Val Val Asn Leu Trp Gly Tyr His Leu Thr Val Lys Ser
            435                 440                 445

Ile Glu Glu Lys Gly Lys Val Val Asp Tyr Gln Val Asp Ile Lys Cys
        450                 455                 460

Asp Val Glu Glu Val Leu Arg Tyr Ser Arg Ala Lys Thr Thr Asn Ala
465                 470                 475                 480

Gly Lys Arg Asn Met Ala Pro Thr Leu Pro Asn Pro Leu Arg Asn Glu
                485                 490                 495

Leu Val Ser Lys Gln Lys Leu Ala Glu Leu Ser Ser Ile Ile Asp Gly
            500                 505                 510

Glu Phe Glu Pro Ile Gln Arg Lys Ala Pro Ser Pro Arg Gly Arg Leu
        515                 520                 525

Gly Arg Arg Val Lys Leu Arg Lys His Leu Val Glu Ile Asn Ala Asp
    530                 535                 540

Glu Ile Thr Ile Thr Leu Ser Arg Tyr Thr Ser Pro Glu Ala Leu Glu
545                 550                 555                 560

Arg Ser Ile Thr Ala Leu Ala Ala Met Thr Gly His Ala Pro Ser Ser
                565                 570                 575

Ile Lys Glu Glu Cys Val Glu Leu Ile Asp Lys Leu Asp Trp Leu Arg
            580                 585                 590

Val Glu Asn Asp Val Ile Gln Tyr Pro Thr Leu Ser Lys Leu Leu Glu
        595                 600                 605

Leu Tyr Asn Ser Gln Asn Glu Ser Lys His Leu Ser Ile Glu Lys Leu
    610                 615                 620

Ile Ala Gly Leu Ala Val Arg Arg Lys Val Cys Lys Leu Val Gln Asp
625                 630                 635                 640

Gly His Ile Asp Glu Thr Val Tyr Arg Ala Leu Asp Glu Met Ala Ala
                645                 650                 655

Gly Ala

<210> SEQ ID NO 3
<211> LENGTH: 135
<212> TYPE: DNA
<213> ORGANISM: Vibrio cholerae
<220> FEATURE:
<221> NAME/KEY: CDS
<222> LOCATION: (112)..(246)

<400> SEQUENCE: 3
tcacttattt acaatgtaaa gccacgtttt gaagtgatga tgaataaata aaagcgagcc    60
gtaagcggaa cgattaaacc gagccactaa gttacggtga atgccattct gattgaaatg   120
atgcgcagga ttcaa                                                    135

<210> SEQ ID NO 4
<211> LENGTH: 345
<212> TYPE: DNA
<213> ORGANISM: Vibrio cholerae
<220> FEATURE:
<221> NAME/KEY: CDS
<222> LOCATION: (767)..(1111)

<400> SEQUENCE: 4
cactcaggtt gtggataaac tgtgtgagca ccttgatcat gcttagaagc ttacgttgat    60
cattgattct gttgactgat gatcatgctt agaggaacaa atgatcatgc tttcgatctt   120
```

| gtattgatca tggtttccat cgatacatga tcatgcttct gaatggctta aaataatctc | 180 |
| ttttaattac aataaattag aactaaaaat cgtcacagat cattagatca ctctaatcat | 240 |
| atttaatcat ttaaatcaga aagatcagtt atttaaaaac aacaaatttt tcttatttta | 300 |
| tgatctcttt ttctttattc tcttggaact atagtgatat tacgg | 345 |

<210> SEQ ID NO 5
<211> LENGTH: 343
<212> TYPE: DNA
<213> ORGANISM: Vibrio vulnificus
<220> FEATURE:
<221> NAME/KEY: CDS
<222> LOCATION: (1,272,585)..(1,272,927)

<400> SEQUENCE: 5

| tctcaccgct gtggataagt tgtttactca tcatgatcat gctttccttc ttacgttgat | 60 |
| cacgcttgcg cattcatgat gatcatcttt acgtctcggt ttgatcatgt tttcgcagtc | 120 |
| tatatgatca tgctttctgg attattatga tcatgcttcc tagatggtaa aaataaacct | 180 |
| tttgttttac agtaagttac tagcaattcc gccgctagat caatagatca tataatcaat | 240 |
| taagatcaga ttaatcaaaa agatcagtta tttaaaaaca agcttttttc tttatttatg | 300 |
| atctattttt ctttatcctc ttggaactat agcgctttta cgg | 343 |

<210> SEQ ID NO 6
<211> LENGTH: 345
<212> TYPE: DNA
<213> ORGANISM: Vibrio harveyi
<220> FEATURE:
<221> NAME/KEY: CDS
<222> LOCATION: (540)..(884)

<400> SEQUENCE: 6

| gctaggatct gtggataagt tgtacaaaca tcatgatcat cgtttcaagg ctgttttgat | 60 |
| catcttttca gaaacttaat gatcatgctt acgacgtttt gtgatcatgc tttccggctc | 120 |
| atgttgatca tcgtttcgat ataatcatga tcatagttcc gttaatgaac ttttaaatat | 180 |
| cattataaaa caaaaactta cagagctaaa atctccaga tcattagatc atataatcaa | 240 |
| ttaagatcag aataatcaga aagatcagtt atttaaaaac ccaagatttt tctttattt | 300 |
| atgatctgtt tttctttatc cttcggaacc atagcaaaac tacgg | 345 |

<210> SEQ ID NO 7
<211> LENGTH: 344
<212> TYPE: DNA
<213> ORGANISM: Vibrio parahaemolyticus
<220> FEATURE:
<221> NAME/KEY: CDS
<222> LOCATION: (785)..(1128)

<400> SEQUENCE: 7

| acggatttct gtggataacc tgtacagaca tcatgatcat cgtttcatga ttgttttgat | 60 |
| catcttttca ggaacttaat gatcatgctt gcggaatgaa gtgatcatgc tttcaaggtt | 120 |
| ttgttgatca tcgtttcggt aaagctatga tcatagttcc gaaacacctc aaaaaaatac | 180 |
| tatttaataa cagtcgctta ggttcgtaaa ataaccaga tcaatagatc atataatcaa | 240 |
| ttaagatcag aataatcaaa aagatcagtt atttaaaaaa caagattttt tctttattta | 300 |
| tgatctgttt ttctttattc ttcggaacca tagcacaact acgg | 344 |

-continued

<210> SEQ ID NO 8
<211> LENGTH: 322
<212> TYPE: DNA
<213> ORGANISM: Vibrio fischeri

<400> SEQUENCE: 8

| | | | | | |
|---|---|---|---|---|---|
| tagaaattct | gtggataact | tgtgtttaga | ccatgatcat | tcttcaataa | aactcatgat | 60 |
| catcgattca | aatggacgat | gatcatgctt | ttgagattta | atgatcattg | atccagagtc | 120 |
| ataatgatca | tgctttcatg | cgtttatttt | tttaattctt | tattttcagt | tacttaaaag | 180 |
| caaaaaacca | accagatcat | agatcaatat | aatcatatag | atcagaatta | atcataaaga | 240 |
| tcagtttaaa | agaataataa | ttttttttctt | tctttaaaga | tccatttcca | ttaacctata | 300 |
| cgaaagaatg | attaaaatac | aa | | | | 322 |

<210> SEQ ID NO 9
<211> LENGTH: 438
<212> TYPE: DNA
<213> ORGANISM: Vibrio cholerae
<220> FEATURE:
<221> NAME/KEY: CDS
<222> LOCATION: (283)..(720)

<400> SEQUENCE: 9

| | | | | | |
|---|---|---|---|---|---|
| taggtatcac | cgaaacgatg | atcaagagca | gcagcttgat | cattcttccg | taaaaaatag | 60 |
| agggttaagg | aaacatgatc | aagagctcat | catggctatg | agtcgaggca | agagaattaa | 120 |
| caattgaaga | tcttcaatcg | gatcgatgat | caagaggtaa | atcgtcgcgg | aagcatgtaa | 180 |
| attcattatc | aatttacggt | cgatgtcagg | cagagtaagg | ctttggctag | tcagtgatga | 240 |
| aaaaccgtct | atcctaacaa | gtctcagtca | aacaagata | aacagaacaa | cagccatgat | 300 |
| catgctttcg | taatcccgct | ccgtcacctt | ggccagcgca | atatggcgct | aagatgtca | 360 |
| attggaagca | caagtcacaa | gtattcattg | cgatatggcc | aagaaatcat | cctctcttga | 420 |
| tcatctttcc | gtggtcat | | | | | 438 |

<210> SEQ ID NO 10
<211> LENGTH: 439
<212> TYPE: DNA
<213> ORGANISM: Vibrio vulnificus
<220> FEATURE:
<221> NAME/KEY: CDS
<222> LOCATION: (1,272,106)..(1,272,544)

<400> SEQUENCE: 10

| | | | | | |
|---|---|---|---|---|---|
| tttatgtctc | tggaagaatg | atcaagtgat | gctttaatca | ttcttcctga | taatgagccg | 60 |
| ttatcgaaac | gatgatcatg | ggaattcata | ctgtaaaata | ggccttccga | tgatggcgtt | 120 |
| aatgatcctt | ataatacgga | aagatgatca | agtagcgatg | gattcggaag | catgaaaaaa | 180 |
| tatcactaag | ttacggtcaa | atgcagatag | aacgggagat | caagctcgtt | tggctcaatt | 240 |
| catcatctag | tgagattggc | tttcagatta | gaatattgac | cttgatatgc | cgtgatcatg | 300 |
| ctttcgtatt | ttctcaatga | aatagcgatg | aaagacaaga | agatagattt | gctgattgtt | 360 |
| tagccaaact | cagcgagaat | tgcggaaaaa | acattcgcat | cctgacaaac | aagctttatg | 420 |
| atgatcatgc | ttccgtctg | | | | | 439 |

<210> SEQ ID NO 11
<211> LENGTH: 441
<212> TYPE: DNA
<213> ORGANISM: Vibrio harveyi

<220> FEATURE:
<221> NAME/KEY: CDS
<222> LOCATION: (47)..(487)

<400> SEQUENCE: 11

| | | | | | |
|---|---|---|---|---|---|
| tgaaatgaag | cggaagtatg | atcaagggga | gttcttgatc | atacttccgg | tactcacacc | 60 |
| aaaatcgaaa | gcatgatcaa | ggaaatcaac | gcatcattta | cattgcagct | cgttttttca | 120 |
| aacggatcaa | tttaccggaa | aaatgatcaa | gtgaattaac | cactcggaag | catgtaattc | 180 |
| tcaagctaat | ttacggaaga | atgcagacag | actgggggat | agaggcaaaa | acgaatataa | 240 |
| aatcacggaa | cgatgaaaac | aaagcgaatg | caaaatgtag | aaactcatct | gatgatcatg | 300 |
| cttccgttta | attaacgcta | atcattaata | agaggcacaa | ccagcaaagt | agagtaagtt | 360 |
| ttcatcacat | gcgcaaataa | tatccaactc | aatgaacaga | acgataaaaa | acctctctyt | 420 |
| tgatcatcga | tgagccgagt | g | | | | 441 |

<210> SEQ ID NO 12
<211> LENGTH: 443
<212> TYPE: DNA
<213> ORGANISM: Vibrio parahaemolyticus
<220> FEATURE:
<221> NAME/KEY: CDS
<222> LOCATION: (294)..(736)

<400> SEQUENCE: 12

| | | | | | |
|---|---|---|---|---|---|
| gaataagaac | ggaaccatga | tcaaggaaga | ctcttgatca | tgttttcgaa | gataactgta | 60 |
| aatacgaaag | catgatcatg | gcagataatg | gacgaatgaa | ggtaaatcaa | ggcttgagta | 120 |
| catggatcca | tttctcggaa | aaatgatcaa | gcaagtaggt | ttctcggaag | catgcttttt | 180 |
| aatgcgctat | ttacggctga | gtgcagacgg | aatgggggat | tgacgcataa | atgcgcctct | 240 |
| caaccttcgg | aacgatgaaa | tacagtatcg | gcaaacaaga | catagtgtct | ttcatgatca | 300 |
| tgcttccgtt | aattctgata | atcatgcaat | cttggaggcc | aaggaccaaa | attgacgtca | 360 |
| ttttaatcgt | ttggctaatt | tggcaacaat | tgaaggtaaa | gagagatgaa | ataaccttag | 420 |
| cttgatcatt | gatccacaac | ctc | | | | 443 |

<210> SEQ ID NO 13
<211> LENGTH: 448
<212> TYPE: DNA
<213> ORGANISM: Vibrio fischeri

<400> SEQUENCE: 13

| | | | | | |
|---|---|---|---|---|---|
| cttaaaaatt | tcgatgtaat | ataagagata | tacttgggtc | tatttccatc | ttatctgagt | 60 |
| aaaatagaag | catgatcaag | gggtatattc | cacaaataaa | caggtgtaaa | ttgataaaat | 120 |
| gtaagttctc | agctaagaag | catgatcaag | caataaatag | cttcggaagc | atgtatcttt | 180 |
| ctttctaaat | tacagaggat | gtatatctga | taaggcttca | gagaagatca | acgaaaaaat | 240 |
| caaataattc | actcaggttg | atctaagaag | aatggtactt | gatcattctt | ctgaaatacg | 300 |
| attaaaacgc | attagactta | agatcatctt | aattttatag | ctattaatga | attaaaaacg | 360 |
| tattttcgga | ctaattaaaa | acgtattttc | ggactaatct | tggtcttaa | atgtcatcca | 420 |
| tcaataaaag | acacctctca | aaagggga | | | | 448 |

VIBRIONACEAE REPLICATION FACTORS AND METHODS OF USE THEREOF

RELATED APPLICATION

This application claims the benefit of provisional application 60/496,791 filed Aug. 21, 2003 in the U.S. Patent and Trademark Office, and which is incorporated herein by reference in its entirety.

GOVERNMENT FUNDING

The invention was made in part with funding from the National Institutes of Health (NIAID, Grant No. A142347). The government has certain rights in the invention.

FIELD OF THE PRESENT INVENTION

The invention relates to compositions useful in modulating DNA replication in a family of pathogenic bacteria, to methods of obtaining inhibitors of DNA replication, and compositions and methods for treating infectious disease caused by these bacteria.

BACKGROUND

The gram-negative bacterium *Vibrio cholerae* causes cholera, a severe and sometimes lethal diarrheal disease. The genomes of *Vibrio cholerae* and related *Vibrio* species are distributed between two circular chromosomes, chromosome I (chrI) and chromosome II (chrII). Origins of replication of the two *Vibrio cholerae* chromosomes are undefined, and mechanisms regulating DNA replication in *Vibrio cholerae* were unknown.

The family Vibrionaceae, of which *V. cholerae* is the most clinically important member, includes several other human and fish pathogens such as *Vibrio parahaemolyticus, Vibrio vulnificus, Photobacterium damselae,* and *Listonella anguillarum,* and is one of the predominant families of marine microorganisms (Kita-Tsukamoto et al., 1993). The genomes of *V. cholerae* and several related *Vibrio* spp. are distributed between two circular chromosomes (Trucksis et al. 1998 and Yamaichi et al. 1999). This genomic structure was originally believed to be unusual among bacteria; it is now clear that many bacterial genomes—including those of several pathogens (e.g., DelVecchio et al., 2002)—consist of more than one chromosome.

*Escherichia coli,* which contains a single circular chromosome, has been the primary model organism used to elucidate mechanisms that control bacterial chromosome replication. Replication in *E. coli* initiates from a specific region of the chromosome, termed oriC. This 258 bp stretch of DNA is capable of autonomous replication and contains recognition sites for several replication factors (Messer et al., 1996). DnaA, the initiator protein, binds to 9 bp repeats within oriC, termed DnaA boxes (Fuller et al., 1984). This interaction stimulates DNA duplex separation at an adjacent region consisting of three AT-rich repeats, resulting in the formation of an open complex (Bramhill et al., 1988). DnaA is also believed to recruit a helicase, DnaB, to the open complex to fully unwind the strands (Marszalek et al., 1994). Once this prepriming complex is formed, RNA primers are synthesized and replication proceeds bidirectionally around the chromosome.

Initiation of replication in *E. coli* is a highly regulated event that occurs only once per cell cycle (Boye et al., 2000). Several mechanisms are thought to control initiation in *E. coli*. First, the methylation state of oriC regulates initiation (Boye et al. 1990 and Marinus 1996). oriC contains eleven sites for methylation by the enzyme DNA adenine methyltransferase (Dam). Ordinarily, *E. coli* DNA is fully methylated. However, newly replicated oriC is hemimethylated and becomes transiently unavailable for reinitiation because it is sequestered by SeqA, a protein that preferentially binds to hemimethylated DNA (Lu et al., 1994). Second, the availability of DnaA (amount of protein per cell) controls initiation, because it is titrated by binding to several high-affinity sites around the chromosome and thereby made unavailable for binding to oriC (Kitagawa et al., 1996). Third, the initiation potential is controlled by regulation of the activity of DnaA (Katayama et al., 1998).

Virtually nothing is known regarding replication control in prokaryotic organisms with multiple chromosomes. The genome of *V. cholerae* is distributed unequally between its two chromosomes; chromosome I (chrI) is larger than chromosome II (chrII) and contains most but not all of the genes essential for *V. cholerae* growth (Heidelberg et al., 2000). The presence of essential genes on chrII indicates that it is a bona fide chromosome as opposed to a dispensable plasmid. Bioinformatic analyses revealed that the putative origin of replication of chr I has sequence similarity to the origin of replication of the *E. coli* chromosome, oriC (Heidelberg et al., 2000). In contrast, the putative origin of replication of chr II lacks similarity to known origins and was assigned solely on the basis of GC nucleotide skew analysis (Heidelberg et al., 2000).

SUMMARY OF THE INVENTION

The invention is based in part on the discovery of compositions that modulate DNA replication in the Vibrionaceae family of bacteria. Identified herein are two *Vibrio cholerae* genes, rctA and rctB, which are critical for *Vibrio* chromosomal replication, particularly for replication of chrII.

In one aspect, the present invention provides an isolated nucleic acid of SEQ ID NO: 1, or the complement of this nucleic acid. The term "complement" as used herein refers to standard Watson-Crick base pair hydrogen-bond rules of base pairing, in which substantially all of the nucleotides of the sequence of the complement, for example, at least about 60%, at least about 70%, at least about 80%, about 90%, about 95%, or about 98%, will form appropriate hydrogen bonds with the sequence.

Also provided is an isolated polypeptide encoded by SEQ ID NO: 1, wherein the polypeptide is capable of modulating replication of DNA in a bacterium. As generally used herein, the terms "modulating," "modulation," and "modulate" include both the processes of increasing DNA replication and of decreasing, i.e., inhibiting, DNA replication. Replication in general means initiation of chromosomal replication, rather than the DNA synthesis that occurs throughout the chromosome, which herein is referred to as "synthesis" or "elongation". In embodiments of the invention, the bacterium is a Gram negative bacterium, in particular, a member of the family of Vibrionaceae, e.g., a member of the genus *Vibrio,* such as *V. cholerae, V. vulnificus, V. fischeri, V. parahaemolyticus, V. anguillarum,* or *V. harveyi.*

In embodiments of the invention, the DNA whose replication is modulated is *V. cholerae* chromosome II, or a portion thereof. As used herein, "portion" includes any fragment or other part of the DNA that is less than the complete DNA sequence. In embodiments of the invention, the portion of the *V. cholerae* chromosome II includes the oriCII$_{vc}$. In some embodiments, this DNA is hemi-methylated DNA. Hemi-methylated DNA includes any DNA that contains one or more methylated bases (e.g., adenine methylated by DNA adenine methyltransferase) but is not fully methylated. By way of non-limiting example, hemi-methylated DNA includes between about 1% methylated DNA and about 25% methylated DNA.

In another aspect, the invention provides an isolated polypeptide comprising the amino acid sequence of SEQ ID NO: 2. In embodiments, the polypeptide is capable of modulating replication of DNA in bacteria. The term "polypeptide" means a sequence of amino acids connected by peptide bonds, and includes the term "protein".

In a further aspect, the invention provides an isolated nucleic acid including SEQ ID NO: 3, or the complement thereof. The nucleic acid is DNA. Alternatively, the nucleic acid is RNA, or is a peptide nucleic acid which is resistant to degradation by nucleases. In embodiments of the invention, the nucleic acid is a modified nucleic acid. Modified nucleic acids are exemplified by having a cytostatic or cytotoxic agent conjugated covalently to the nucleic acid.

In another embodiment, the invention provides a method of screening for an antibacterial agent capable of inhibiting chromosome replication in a cell of a bacterial species of the family of Vibrionaceae. The method includes contacting a test cell with a putative agent; measuring replication of a nucleic acid in the test cell; and, comparing the replication with replication in a control cell not so contacted with the agent, whereby a decrease in the replication in the test cell relative to the replication in the control cell identifies the agent as being capable of inhibiting DNA replication in the bacterial cell. The nucleic acid replication can be measured by one of ordinary skill in the art using routine procedures, including measurement of cell growth such as turbidometrically or calorimetrically; specific activity of a cell enzyme, for example, one capable of cleavage of a calorimetric substrate; incorporation of a radiolabel such as $^3$H-thymidine into DNA, collected for example as a tricloracetic acid precipitate of macromolecules; and cell content of a gene on chromosome II of the cell, for example, by use of PCR using probes specific for markers on chromosome II.

The bacterial cell is a member of the family of Vibrionaceae. Groups of exemplary bacteria include *Aeromonas, Allomonas, Beneckea, Enhydrobacter, Listonella, Lucibacterium, Photobacterium, Plesimonas, Salinivibrio,* and *Vibrio*. In embodiments of the invention, the bacterial cell is a pathogen, for example, a human pathogen, a fish pathogen, or a shellfish pathogen. The identified agent is bacteriostatic, meaning that it prevents bacterial growth, for example, by inhibition of initiation of chromosome replication or cell division. In other embodiments, the identified agent is bactericidal, meaning that it causes bacterial cell death.

The invention further provides a method of screening for an agent, the method including contacting a Vibrionaceae test bacterial cell with a putative agent; measuring the test rate of proliferation the bacterial cell; and comparing the test rate of proliferation with the rate of proliferation of a control bacterial cell not so contacted with the putative agent, whereby a decrease in the rate of proliferation of the test bacterial cell relative to the rate of proliferation of the control bacterial cell identifies the agent as being capable of inhibiting DNA replication in a bacterial cell.

The present invention includes a method of inhibiting DNA replication in a bacterium by contacting the bacterium with the identified agent. The present invention further includes a method of treating a patient having an unwanted bacterial cell such as a cell of a bacterium in the family Vibrionaceae, for example, a patient suffering from cholera by contacting the patient with the identified agent.

In another aspect, the present invention includes a method of inhibiting DNA replication in a bacterium, such as a member of the Vibrionaceae, by contacting the bacterium with an isolated nucleic acid comprising SEQ ID NO: 3, or the complement thereof.

In a further aspect, the present invention includes a method of inhibiting proliferation of a bacterium, such as a member of the Vibrionaceae, by contacting the bacterium with an isolated nucleic acid comprising SEQ ID NO: 3, or the complement thereof.

In a another aspect, the present invention includes a method of inhibiting DNA replication in a bacterium, such as a member of the Vibrionaceae, by contacting the bacterium with an isolated nucleic acid comprising the incompatibility determinant inc, wherein the incompatibility determinant inc is derived from a bacterium of the family of Vibrionaceae. The bacterium is selected from the group consisting of *V. cholerae, V. vulnificus, V. fischeri, V. parahaemolyticus,* and *V. harveyi*.

In a another aspect, the present invention includes a method of inhibiting DNA replication in a bacterium by contacting the bacterium with an isolated nucleic acid comprising the *Vibrio cholerae* chrII incompatibility determinant inc.

The present invention also provides a method of treating a patient suffering from cholera by administering to the patient a nucleic acid comprising the *Vibrio cholerae* chrII incompatibility determinant inc.

The present invention further includes a method of treating a patient suffering from an unwanted bacterium such as a member of the Vibrionaceae, for example, a patient with cholera, by administering to the patient a nucleic acid comprising SEQ ID NO:3, or the complement thereof.

The present invention further includes a method of treating a patient having an unwanted cell of a Vibrionaceae by administering to the patient a nucleic acid comprising the *Vibrio cholerae* chrII incompatibility determinant inc.

In another embodiment, the invention includes a method of treating a patient having an unwanted cell of a Vibrionaceae by administering to the patient the agent identified by the above-described methods.

In another embodiment, the invention includes treating a patient having an unwanted cell of a *Vibrionaceae* by administering to the patient a nucleic acid comprising SEQ ID NO:3, or the complement thereof. In certain embodiments, the bacterium or cell is *Vibrio cholerae.*

The invention further provides a kit for inhibiting growth of a cell of a Vibrionaceae, including a nucleic acid comprising SEQ ID NO: 3 or a complement thereof, and a container. The kit in a related embodiment also includes instructions for use. In embodiments of the invention, the nucleic acid is in an effective dose.

The invention also provides a kit for performing the methods of the invention, that includes a frozen or lyophilized culture of a Vibrionaceae, a container, and instructions for use. Optionally, the kits of the invention include a positive control reagent, such as a known DNA replication inhibitor known to one of skill in the antibiotic arts, e.g., a gyrase inhibitor, capable of inhibiting replication of the Vibrionaceae. Further, the kits of the invention may include reagents for analysis of replication.

An embodiment of the invention herein is use of a nucleotide sequence of a Vibrionaceae origin of replication for a vector. The origins of replication of the two Vibrionaceae chromosomes provided herein can be used to engineer a plasmid as a vector for handling recombinant DNA. For example the Vibrionaceae is selected from the genera *Vibrio*, *Photobacterium*, and *Listonella*. Further, the Vibrionaceae is selected from the group of *Vibrio* consisting of *V. cholerae*, *V. vulnificus*, *V. alginolyticus*, *V. fluvialis*, *V. furnissii*, *V. proteolyticus*, *V. harveyi*, *V. parahaemolyticus*, and *V. fisheri*. The provided sequence in various embodiments encodes oriCI$_{vc}$ or oriCII$_{vc}$.

Also provided is a vector comprising a nucleotide sequence according to any of SEQ ID NOs: 6–10. The vector includes at least one of a Vibrionaceae nucleotide sequence selected from the group of a DnaA box, a 12-mer repeat sequence, an IHF binding site, and an AT-rich 13-mer.

BRIEF DESCRIPTION OF THE DRAWINGS

FIG. 1A is a drawing and bar graph that shows the frequency of exconjugant formation in *V. cholerae* Bah-3. The X in line 7 represents a substitution of 6 bp in the fourth 12-mer repeat in ig2.

FIG. 1B is a drawing and a bar graph that shows the frequency of exconjugant formation in *E. coli* MC4100. The white bars in lines 9 and 10 show the frequency of exconjugant formation when the recipient was MC4100 harboring a plasmid (porf2) expressing rctB. The X in line 10 represents a frame shift at bp 79 of rctB. The black triangles within the small arrows in each of lines 11, 12, and 13, respectively, represent a stop codon at amino acid position (aa) 25, aa 1, and a deletion of bp 21 in rctA, respectively.

FIG. 2A is a schematic representation of the replication origin regions of *V. cholerae* chromosome I and chromosome II. AT-rich regions, DnaA boxes, IHF binding sites, GATC sequences, and small repeats are as indicated in the box. The 11-mer sequence is ATGATCAAGAG (SEQ ID NO: 4) and the 12-mer consensus is (A/T)TGATCATNN (A/T)T (SEQ ID NO: 5; see FIGS. 7 and 8). Hatch marks reflect 100 bp intervals, but open reading frames at the ends of each ori are not to scale. The lines below each construct represent probes used in gel shift experiments. The minimal oriCII$_{vc}$ as defined in FIG. 1A is shown above the oriCII$_{vc}$ region within the bracket on the right above the map.

FIG. 2B is a set of photographs of autoradiographs of gel shift experiments. Triangles represent increasing concentrations (0 ng negative control, 56 ng, 113 ng, 225 ng, 450 ng, and 900 ng) of His$_6$-tagged RctB. Roman numerals beneath each autoradiograph represent the probes as shown in FIG. 2A.

FIG. 2C is a set of photographs of Southern analyses of chromosomal DNA digested with HindIII and probed with rctB. Lanes 1–13 and 17 are from species within the family Vibrionaceae (1, *V. cholerae* N 16961; 2, *V. parahaemolyticus*; 3, *V. alginolyticus*; 4, *V. fluvialis*; 5, *V. vulnificus*; 6, *V. furnissii*; 7, *V. proteolyticus*; 8, *Photobacterium damselae*; 9, *P. leiognathi*; 10, *Listonella anguillarum*; 11, *V. fischeri*; 12, *V. harveyi*; 13, *P. phosphoreum*; 17, *V. cholerae* N16961). Lanes 14 and 16 are *Plesiomonas shigelloides* and *E. coli* MC1061, respectively, from the family Enterobacteriaceae, and lane 15 is *Aeromonas hydrophila* from the family Aeromonadaceae.

FIG. 6A shows the replication capacity of construct pJEL109 (Lobner-Olesen et al., 1992) (miniR1, a dam-independent plasmid) in the following strains: MC1061 (wild type (wt) E. coli), KO1607 (Δdam), MC1061ΔseqA (ΔseqA), and KO1607ΔseqA (ΔdamΔseqA). Transformation of wild-type or dam E. coli by miniR1 occurred with similar efficiency regardless of the methylation status of the plasmid.

FIG. 6B shows the replication capacity of construct pMR2 (Jensen et al., 1990) (poriC) in the following strains: MC1061 (wild type (wt) E. coli), KO1607 (Δdam), MC1061ΔseqA (ΔseqA), and KO1607ΔseqA (ΔdamΔseqA).

FIG. 6C shows the replication capacity of construct poriCII. The crosses indicate the following strains: methylated poriCII had a relative transformation efficiency of 0.00053 in Δdam and 0.0001 in ΔdamΔseqA, and unmethylated poriCII had a relative transformation efficiency of 0.007 in ΔΔdam and 0.0001 in ΔdamΔseqA.

FIG. 6D shows the replication capacity of construct poriCI in the following strains: MC1061 (wild type (wt) E. coli), KO 1607 (Δdam), MC1061ΔseqA (ΔseqA), and KO1607ΔseqA (ΔdamΔseqA). The asterisks indicate that the relative transformation efficiencies were less than detectable by this assay (<0.0002).

FIG. 7 is a set of nucleotide sequences from V. cholerae (SEQ ID NO.: 4), V. vulnificus (SEQ ID NO.: 5), V. harveyi (SEQ ID NO.: 6), V. parahaemolyticus (SEQ ID NO.: 7), and V. fischeri (SEQ ID NO.: 8) that were aligned using Vector NTI (InforMax). Bases that are conserved among all five species were identified, and bases conserved in at least three were identified. The putative DnaA box, having sequences conserved among all five species, is highlighted by the left-most box on line one, the 12-mer repeats are highlighted by the middle and right-most boxes on line 1 and boxes on line 2, and the AT-rich region's two 13-mers (Messer and Weigel, 1996) are highlighted boxes on lines 4 and 5.

FIG. 8 is a set of nucleotide sequences from V. cholerae (SEQ ID NO.: 9), V. vulnificus (SEQ ID NO.: 10), V. harveyi (SEQ ID NO.: 11), V. parahaemolyticus (SEQ ID NO.: 12), and V. fischeri (SEQ ID NO.: 13) that were aligned using Vector NTI (InforMax). Bases that are conserved among all five species are shown in boxes on lines 1, 2, 7 and left-most box on line 3, and bases conserved in at least three are shown in the box on line 5. The 11-mer repeats are highlighted by boxes on lines 1, 2, 7 and left-most box on line 3, the conserved 13 bp of the incompatibility determinant are highlighted in the box on the right on line 3, and the 12-mer repeat is highlighted in the box on line five.

DETAILED DESCRIPTION OF THE EMBODIMENTS

Figure 1A:
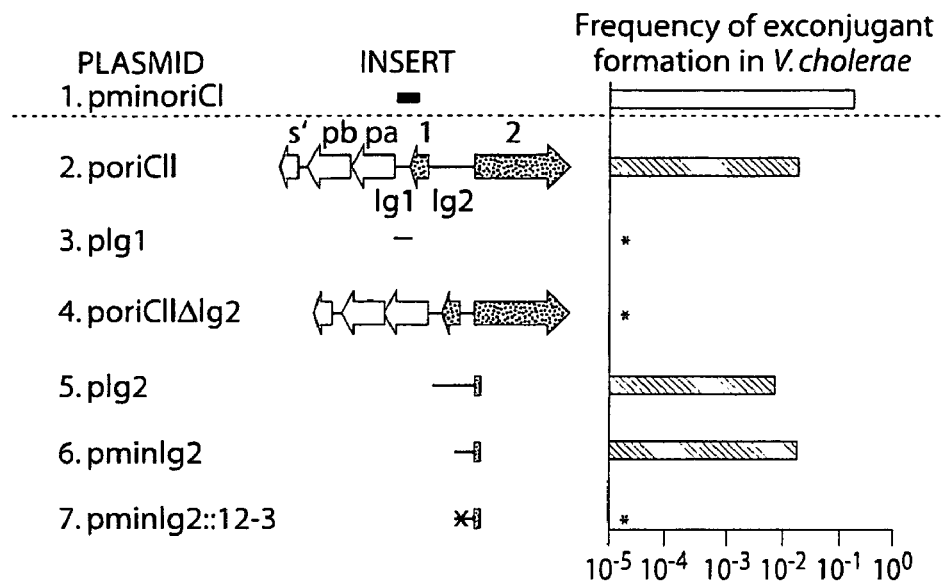
FIGS. 1A and 1B show the delineation of the replication origins of the two *V. cholerae* chromosomes. A conjugation-based assay was used to assess the replication capacity of fragments of chrI and chrII inserted into a conditionally replication-defective vector, pGP704. pGP704-based plasmids were transferred by conjugation from the mob+ donor *E. coli* strain SM10λpir (Miller and Mekalanos, 1988), to *E. coli* MC4100λpir, MC4100, and the recA pir *V. cholerae* strain Bah-3. The frequency of exconjugant formation was calculated by dividing the number of exconjugant colony forming units (cfu) by the number of donor cfu. The plasmid inserts are depicted as arrows for open reading frames and lines for intergenic regions. The insert in pminoriCI corresponds to the oriCI$_{vc}$ intergenic region shown in FIG. 2A. The insert in poriCII consists of 5.8 kb surrounding the previously annotated replication origin of chrII (Heidelberg et al., 2000), designated ig1. This insert includes vca0002 (rctB) (2), vca0001 (rctA) (1), parA (pa), parB (pb), and a fragment of vca1113 (s'). The frequencies shown are means derived from two to four experiments. Asterisks indicate that the frequency of exconjugant formation was below detection (<1.7×10$^{-5}$) by this assay. When pGP704 without an insert was transferred to either Bah-3 or MC4100, no exconjugants were detected.

Details of various embodiments and examples of the invention are found in the publication entitled, "Distinct Replication Requirements for the Two Vibrio Cholerae Chromosomes", by Elizabeth S. Egan and Matthew K. Waldor, to appear in (Aug. 22, 2003; Cell 114(4): 521–530) and which is hereby incorporated herein in its entirety.

EXAMPLES

The following methods were used throughout the Examples.

Plasmid and Strain Construction

DNA from V. cholerae N16961 (Heidelberg et al., 2000) was used as template for PCR amplification of fragments for insertion into pGP704 (Miller and Mekalanos, 1988) to create chrI- and chrII-derived minichromosomes. The insert in poriCI extends from chrI bp 2,956,820 through 1,300 according to the published annotation of the V. cholerae genome sequence (Heidelberg et al. 2000). The insert in poriCII extends from chrII bp 1,069,696 through bp 3,191. All primer sequences are available upon request. Frameshift and substitution mutations were constructed using the QuikChange Site-Directed Mutagenesis Kit (Stratagene), and deletions were constructed using overlap-extension PCR mutagenesis as previously described (Moyer et al., 2001). All mutations were confirmed by DNA sequencing. High-copy plasmids containing $oriCII_{vc}$ or $oriCI_{vc}$ sequences were constructed by amplifying sequences from V. cholerae N 16961 and introducing them into the pUC-based plasmid pCRII-TOPO (Invitrogen). Plasmids pEE481 and pEE482 were constructed by introducing the insert from plasmid p3642-topo (see FIG. 4) into the vector pGZ119 (Lessl et al., 1992) in both orientations. Full-length rctB along with upstream sequence including its ribosome binding site was introduced into the expression vector pGZ119 (Lessl et al., 1992) to create the complementing plasmid porf2. The expression plasmid for production of C-terminal $His_6$-tagged RctB, porf2-BAD, was constructed by inserting the rctB coding sequence into pBAD-topo (Invitrogen). Strain KO1607 is E. coli MC1061 dam13::tn9 (gift of A. Wright). Strains MC1061ΔseqA and KO1607ΔseqA were constructed by P1 transduction of the seqA allele from strain CM735 seqAΔ::tet (Lu et al., 1994) using standard protocols.

Conjugation Assays

Conjugation assays to determine the replication capacity of chrI and chrII-derived minichromosomes were performed by overlaying approximately equal numbers of donor and recipient cells on LB agar plates and incubating for 5 hr at 37° C. Dilutions were plated on selective medium to enumerate donor cfu, recipient cfu, and exconjugant cfu. In experiments with a complementing plasmid in trans, IPTG was added to the medium to induce gene expression. The frequency of exconjugant formation was calculated by dividing the number of exconjugant by donor cfu.

Molecular Biology Methods

Southern hybridization was carried out using horseradish peroxidase-labeled DNA probes, prepared and hybridized using the ECL direct nucleic acid labeling and detection system (Amersham Pharmacia). Genomic DNA was isolated using the Gnome DNA kit (BIO101). Nucleotide alignments were performed using Vector NTI (InforMax). The *V. harveyi* oriCII-region sequence (GenBank AY309011) was determined by sequencing the insert of plasmid pNH26 (Zyskind et al., 1983) using dye terminator cycle sequencing at the Tufts University School of Medicine Core Facility.

DNA Binding Assays

RctB-His$_6$ was affinity purified on Ni-NTA resin (Qiagen) from lysates of *E. coli* RJ3236 (porf2-BAD) grown in the presence of 0.02% arabinose according to the manufacturer's protocol. Probes for gel shift experiments were amplified by PCR from poriCII or poriCI DNA using a $^{32}$P-labeled oligonucleotide. Probes were gel purified. Gel shift reactions (20 µl volume) were performed by incubating 1,000 c.p.m. of each probe with increasing amounts (0 ng, 56 ng, 113 ng, 225 ng, 450 ng, and 900 ng) of purified RctB-His$_6$ in a reaction buffer containing 25 mM Tris-HCl (pH 7.9), 110 mM NaCl, 5.12 mM EDTA, 2 mM DTT, 0.1 mg/ml BSA, and 12.5 µg/ml sonicated salmon sperm DNA for 30 min at room temperature. Reactions were analyzed on 6% DNA retardation gels (Invitrogen).

Rnase Protection Assay (RPA)

RNA was prepared using the Rneasy Kit (Qiagen) from exponentially growing *V. cholerae* N 16961, *E. coli* MC4100 (poriCII), and *E. coli* MC4100 without plasmid, and treated with Dnase I. Yeast RNA was provided in the RPA III kit (Ambion). Riboprobes were synthesized from linearized cloned DNA templates with the Maxiscript kit (Ambion) using 40 µCi of [$^{32}$P]UTP for rpoB and 50 µCi of [$^{32}$P]UTP for rctA. The expected protected fragment sizes were as follows: 132 bp for rctA, 211 bp for *V. cholerae* rpoB, and 1226 bp for *E. coli* rpoB. The corresponding full-length probes were 233 bp, 341 bp, and 1310 bp, respectively. All riboprobes were gel purified on 6% denaturing polyacrylamide gels. RPAs were conducted using the RPA III kit (Ambion) according to manufacturer's instructions using 15 µg total RNA for each sample. Products were separated on 6% denaturing polyacrylamide gels and exposed to film.

Stability Assays

For the stability tests in *V. cholerae*, fresh overnight ampicillin-resistant Bah-3 (Pearson et al., 1993) colonies containing the appropriate plasmid were inoculated into LB broth without ampicillin. The percentage of cfu containing plasmid was determined at times T=0 and T=6 hr after growth without selection by plating equal volumes of bacteria on selective and nonselective media.

Transformation Assays

Transformation experiments were performed with 100 ng of each plasmid using a standard electroporation protocol. Electrocompetent *E. coli* and *V. cholerae* were prepared using standard protocols. For the incompatibility assays involving two plasmids, the cells were prepared with selection for the ampicillin-resistant plasmid. Dilutions were plated on selective medium to determine the number of transformants. Unmethylated pJEL109 and pMR2 were obtained by isolating the plasmids from the dam *E. coli* strain KO1607. We obtained unmethylated poriCII by isolating plasmid from a dam pir$^+$ *E. coli* strain (SM10λpir dam 13::tn9), where replication initiates from the R6K origin of replication.

In various embodiments of the invention herein the origins of replication of the two *V. cholerae* chromosomes are experimentally defined. Novel replicon-specific requirements for each chromosome as well as factors that are required for replication of both chromosomes are provided.

Example 1

Delineation of oriCI$_{vc}$ and oriCII$_{vc}$

To functionally define the genes and sequences required for replication of the two *V. cholerae* chromosomes, minichromosome derivatives of each chromosome were constructed by introducing each annotated (Heidelberg et al., 2000) replication origin into a mobilizable, conditionally replication-defective vector, pGP704 (Miller and Mekalanos, 1988). This vector contains the R6K origin of replication, which requires the product of the pir gene to initiate replication. In pir-deficient strains, pGP704-based plasmids will only replicate if they carry an alternate, functional replication cassette. The ability of the *V. cholerae*-pGP704 chimeric plasmids to replicate autonomously in both pir *E. coli* and *V. cholerae* (recA strain Bah-3 [Pearson et al., 1993]) was measured by quantifying the frequency of exconjugant formation in conjugation assays in which the plasmids were mobilized from a pir$^+$ donor to pir recipients. All of the plasmids tested were able to replicate and form exconjugants in pir$^+$ *E. coli*, showing that their inserts have no negative effect on pGP704 mobility (data not shown).

Figure 1B:
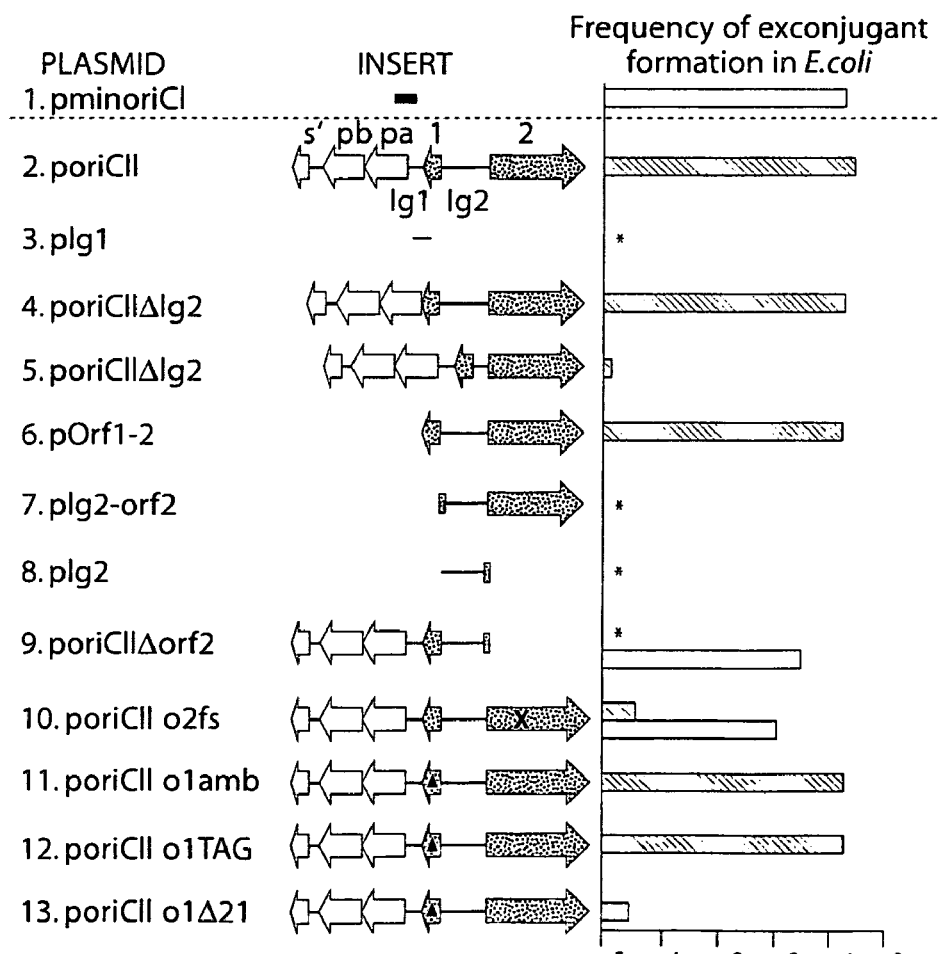

The annotated oriCI$_{vc}$ resides between the genes mioC and gidA (Heidelberg et al., 2000). A 447 bp fragment from this intergenic region replicated in both *V. cholerae* and the surrogate host, *E. coli* (FIGS. 1A and 1B, line 1). This indicates that this fragment contains the minimal oriCI$_{vc}$ and demonstrates that *E. coli* can supply any transacting factors needed for oriCI$_{vc}$-based replication. In contrast, a plasmid (pIg1) containing the intergenic region previously annotated as oriCII$_{vc}$ did not form exconjugants in either *V. cholerae* or *E. coli*, indicating that pIg1 cannot replicate autonomously, i.e., that this intergenic region either does not contain oriCII$_{vc}$ or requires additional sequences in cis for replication (FIGS. 1A and 1B, line 3). A larger minichromosome II, poriCII, replicated in both species (FIG. 1A and 1B, line 2), indicating that oriCII$_{vc}$ and any other sequences required in cis for replication are contained within the 5.8 Kb insert of poriCII. This minichromosome includes two intergenic regions (ig1 and ig2), two hypothetical genes (vca0001 and vca0002), and two genes with homology to plasmid partitioning genes (parA and parB).

Mutational analysis of poriCII confirmed that ig1 is not required for replication in *E. coli* (FIG. 1B, line 4), indicating that the original annotation of ig1 as oriCII$_{vc}$ was incorrect. However, a deletion internal to ig2, the other intergenic region within poriCII, revealed that ig2 includes sequences required for replication in both *V. cholerae* and *E. coli* (FIG. 1A, line 4, and FIG. 1B, line 5). Furthermore, a minichromosome containing only ig2 sequences could replicate in *V. cholerae*, indicating that ig2 contains the true oriCII$_{vc}$ (FIG. 1A, line 5). Only the right side of ig2 was required for pminIg2 to replicate in *V. cholerae*, demonstrating that the minimal oriCII$_{vc}$ is contained within this 406 bp region (FIG. 1A, line 6).

Unlike a plasmid containing only oriCI$_{vc}$ (pminoriCI), pIg2 could not replicate in *E. coli* (FIG. 1B, lines 1 and 8). Instead, derivatives of poriCII required inclusion of the two flanking hypothetical genes, designated vca0001 and vca0002 by Heidelberg et al. (2000), to replicate in *E. coli*

(FIG. 1B, lines 6–10). Given this requirement, these genes have been herein termed vca0001, rctA (replication of chromosome two; SEQ ID NO:3) and vca0002, rctB. For rctB, a gene (SEQ ID NO:1) encoding a predicted protein product of 658 amino acids (aa; SEQ ID NO:2), both deletion and frameshift mutations severely compromised the ability of poriCII to replicate in E. coli, and in both cases the replication defects could be complemented by expressing rctB in trans on another plasmid (FIG. 1B, lines 9–10). In V. cholerae, the RctA and RctB gene products are provided by the chromosome to facilitate pIg2 and pminIg2 replication (FIG. 1A, lines 5–6).

Example 2

Sequence Analysis of oriCI$_{vc}$ and oriCII$_{vc}$

Figure 2A:
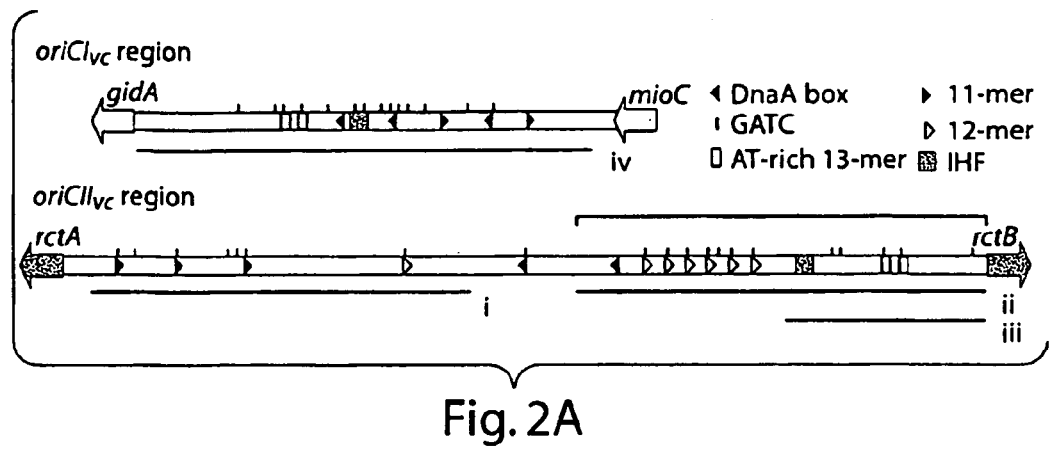
FIGS. 2A–2C are a drawing are photographs that show that RctB binds to oriCII$_{vc}$, but not to oriCI$_{vc}$, and is found in diverse genera in the family Vibrionaceae.

The DNA sequences of both oriCI$_{vc}$ and oriCII$_{vc}$ contain several features also found in E. coli oriC. In fact, the sequence of oriCI$_{vc}$ is very similar to oriC (58% identity). Like oriC, oriCI$_{vc}$ has an AT-rich region, five apparent DnaA boxes, a likely binding site for IHF (a protein that bends DNA), and many potential sites for Dam methylation (GATC sequences) (FIG. 2A). Though the minimal oriCII$_{vc}$ lacks sequence similarity to E. coli oriC, it does contain an AT-rich region, a single putative DnaA box, a putative IHF binding site, and an overrepresentation of GATC sequences (FIG. 2A). In addition, within the entire ig2 region, there are two related repeat sequences, an 11-mer and a 12-mer, a finding reminiscent of replication origins found in iteron-type plasmids, where small repeat sequences are required for both replication and copy number control (Chattoraj 2000 and del Solar et al. 1998) (FIG. 2A).

The available nucleotide sequence databases were searched and sequences similar to ig2 were found in the complete genomes of Vibrio fischeri, Vibrio parahaemolyticus, and Vibrio vulnificus. In addition, ig2-like sequences were found in an insert of a plasmid that was isolated as part of a genetic screen for functional V. harveyi origin sequences (Zyskind et al., 1983). Alignment of V. cholerae oriCII$_{vc}$ with sequences from V. vulnificus, V. fischeri, V. parahaemolyticus, and V. harveyi revealed that the 11-mer repeats, 12-mer repeats, the DnaA box, and the AT-rich region were all conserved (FIGS. 7 and 8). Furthermore, in each species, the 12-mers were spaced 11 bp apart, suggesting that the same DNA sequences would be displayed on the same face of the DNA. The conservation of the 12-mer repeats among five Vibrio species suggests that they are important for chrII replication. An essential replication function for the 12-mer repeats was demonstrated by the finding that substitution of six bp in a 12-mer abolished replication of pminIg2 in V. cholerae (FIG. 1A, line 7).

Example 3 rctB is Conserved and Encodes an oriCII$_{vc}$ Binding Protein

Figure 2B:
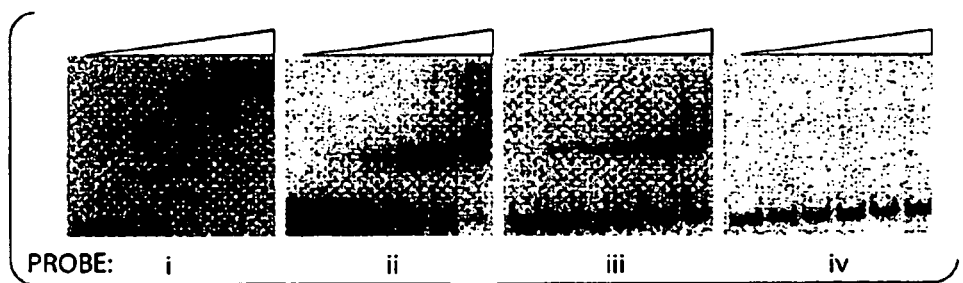
Figure 2C:
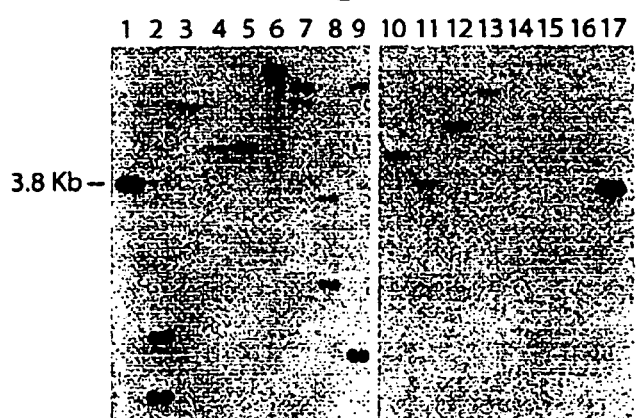

Orthologs of RctB were searched and found in V. vulnificus, V. fischeri, V. parahaemolyticus, and V. harveyi (identity >74%; data not shown). Southern analysis revealed that rctB is present in diverse genera in the family Vibrionaceae, suggesting that the presence of two chromosomes may be a defining feature not just of the genus Vibrio but of the widespread family Vibrionaceae (FIG. 2C). In V. cholerae, all attempts to isolate mutations that inactivate rctB were unsuccessful, consistent with a conclusion that rctB is an essential gene.

As rctB is required in replication of poriCII, and replication factors often act at origins, RctB binding to oriCII$_{vc}$ was investigated. Recombinant epitope-tagged RctB was expressed in E. coli, purified, and used in gel shift experiments with probes derived from oriCII$_{vc}$ and oriCI$_{vc}$. Several different probes spanning ig2 were bound by RctB, but an oriCI$_{vc}$ probe was not (FIG. 2B, i–iv). With a probe derived from the left side of ig2, multiple shifted species were observed (FIG. 2B, i), indicating that this region contains multiple RctB binding sites.

Example 4 rctA Encodes an RNA Required for oriCII$_{vc}$-Based Replication

Figure 3:
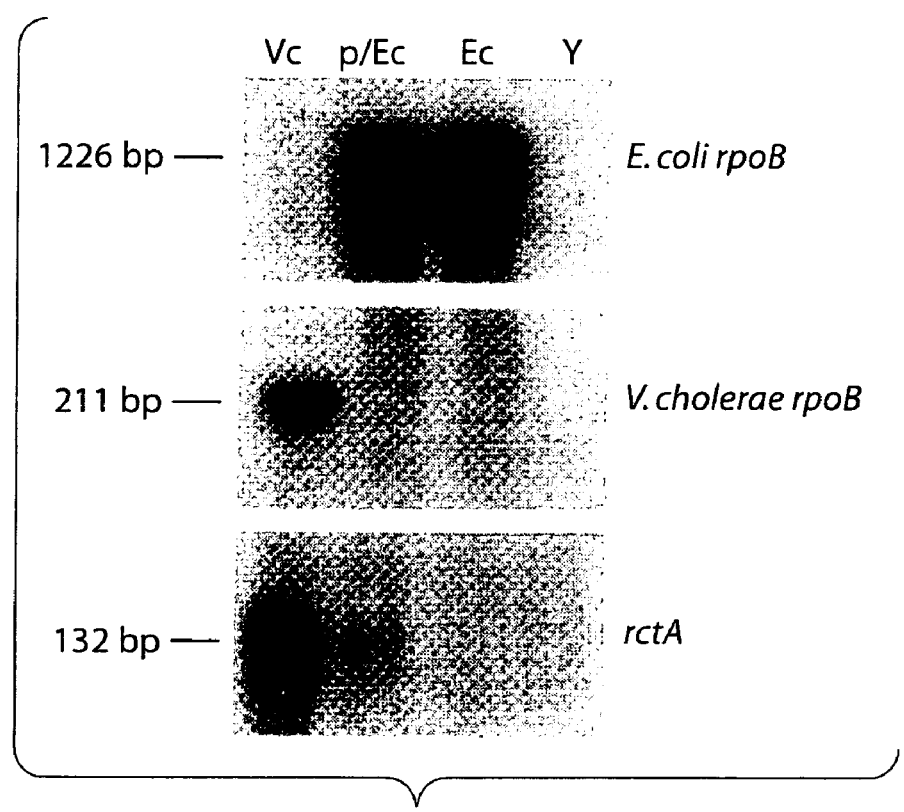
FIG. 3 is a set of photographs of gel analyses of results from an assay for detection of RctA RNA in *V. cholerae* and poriCII-containing *E. coli*. A ribonuclease protection assay was used to detect rctA transcripts using an antisense RNA probe spanning the entire annotated vca0001 (rctA) gene. Probes for *E. coli* and *V. cholerae* rpoB transcripts were used as controls. The rctA autoradiograph was exposed for 53 hr and the rpoB autoradiographs were exposed for 5 hr. RNA was prepared from the *V. cholerae* strain N16961 (Vc) and the *E. coli* strains poriCII/MC4100 (p/Ec) and MC4100 without plasmid (Ec). Yeast RNA (Y) was used as a negative control. The sizes of the protected bands are shown to the left of the figure.

Analysis of poriCII revealed that the gene vca0001 (rctA) is required for oriCII$_{vc}$-based replication (FIG. 1B, lines 6 and 7). Further studies indicated that an RNA transcribed from this region was the required replication factor. A substitution mutation in poriCII that changed a putative RctA amino acid 25 (of 44 predicted aa) to an amber stop codon (poriCII 01amb) did not affect replication (FIG. 1B, line 11). Similarly, replacement of the putative start codon of rctA with a stop codon did not prevent autonomous replication of the plasmid, poriCII 01TAG, in E. coli (FIG. 1B, line 12). These data, together with the fact that there are no other potential start codons within rctA, indicate that a protein is not required for poriCII replication translated from rctA. Since pIg2 and pminIg2, which do not contain rctA in cis, replicate in V. cholerae, rctA is not a required cis-acting sequence. Together, these results suggest that a candidate product of this gene is a functional RNA. We confirmed that RNA is transcribed from rctA in both V. cholerae and poriCII-containing E. coli by performing a ribonuclease protection assay (RPA), using a probe complementary to rctA (FIG. 3). The entire probe was found to be protected, suggesting that the active species encoded by this region is at least 132 bp, and potentially longer. Surprisingly, a single base pair deletion in rctA, at position 21, did inhibit replication of poriCII (FIG. 1B, line 13). This finding confirms the requirement for rctA, and indicates that this base pair may be important in RNA structure.

Example 5

Identification of a chrII Incompatibility Determinant

Figure 9:
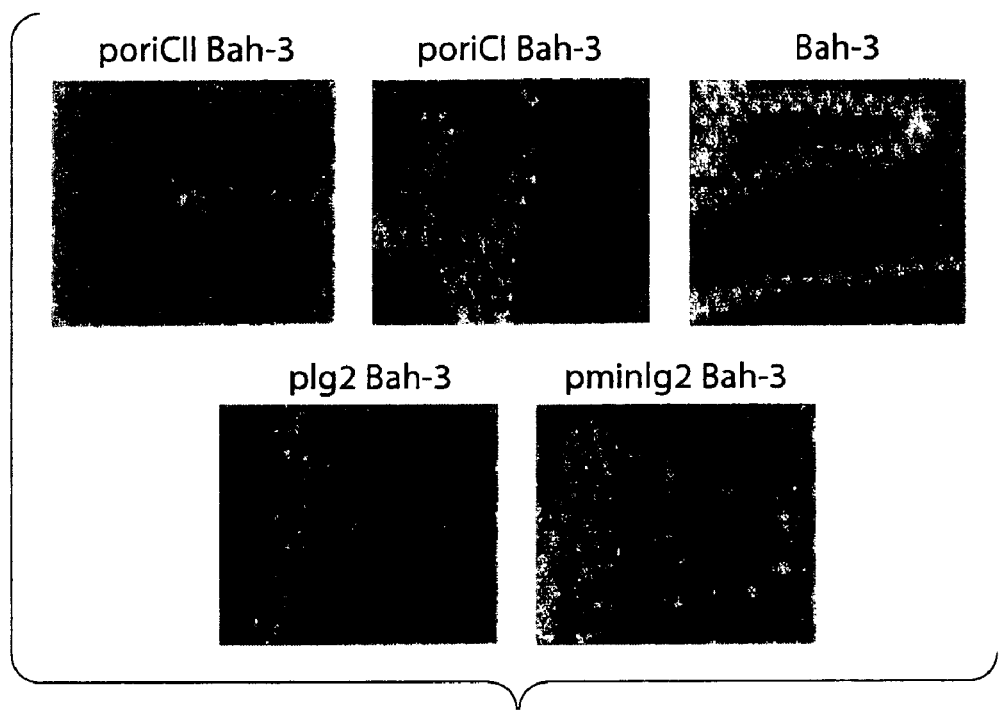
FIG. 9 is a photograph of Petri plates that shows V. cholerae Bah-3 cells harboring the ampicillin-resistant plasmid poriCII, poriCI, pIg2, or pminIg2 (see FIG. 1). Cells were streaked on ampicillin-containing LB-agar and grown overnight at 37° C. Bah-3 cells without plasmid were streaked onto streptomycin-containing LB-agar and grown overnight at 37° C. Pictures were taken with a digital camera at the same magnification.

V. cholerae cells containing poriCII formed smaller colonies than did cells containing poriCI or no plasmid (FIG. 9). This phenotype was not attributable to coding regions in poriCII, as cells containing pIg2 (which lacks coding sequences) also formed small colonies (FIG. 9). Furthermore, only a portion of ig2 accounts for this phenotype, as cells with pminIg2, a plasmid that only includes the minimal oriCII$_{vc}$, formed normal-sized colonies (FIG. 9). Colonies formed by E. coli containing poriCII or poriCI were indistinguishable from each other and from cells without plasmid. These findings suggested that a plasmid-borne copy of a region on the left side of ig2, outside of the minimal oriCII$_{vc}$, restricted V. cholerae growth in the presence of selection for the plasmid. This impairment may result from instability of plasmids containing this region or from an inhibitory effect of this region on chrII replication. The percentage of V. cholerae cells retaining pIg2 fell more than 2000-fold during a six-hour growth period in the absence of antibiotic selection (Table 1). In contrast, pmInIg2 was relatively stably maintained (Table 1). The profound difference in the stability of pmInIg2 and pIg2 suggests that the left side of ig2 renders pIg2 unstable in *V. cholerae*, but is also consistent with ig2-mediated inhibition of chrII replication leading to a large selective advantage for cells that lose the plasmid. Together, these results indicate that the small colony phenotype was attributable to antibiotic-mediated killing of cells without plasmid, likely reflecting incompatibility between pIg2 and one or both of the *V. cholerae* chromosomes.

TABLE 1 pIg2 Is Unstable in *V. cholerae*

| Plasmid[1] | Frequency of Amp Resistance[2] | | Fold Decrease[3] |
|---|---|---|---|
| | T = 0 | T = 6 hours | |
| pIg2 | $3.9 \times 10^{-2}$ | $1.8 \times 10^{-5}$ | 2167 |
| pmInIg2 | $2.7 \times 10^{-1}$ | $2.0 \times 10^{-2}$ | 14 |

Figure 4:
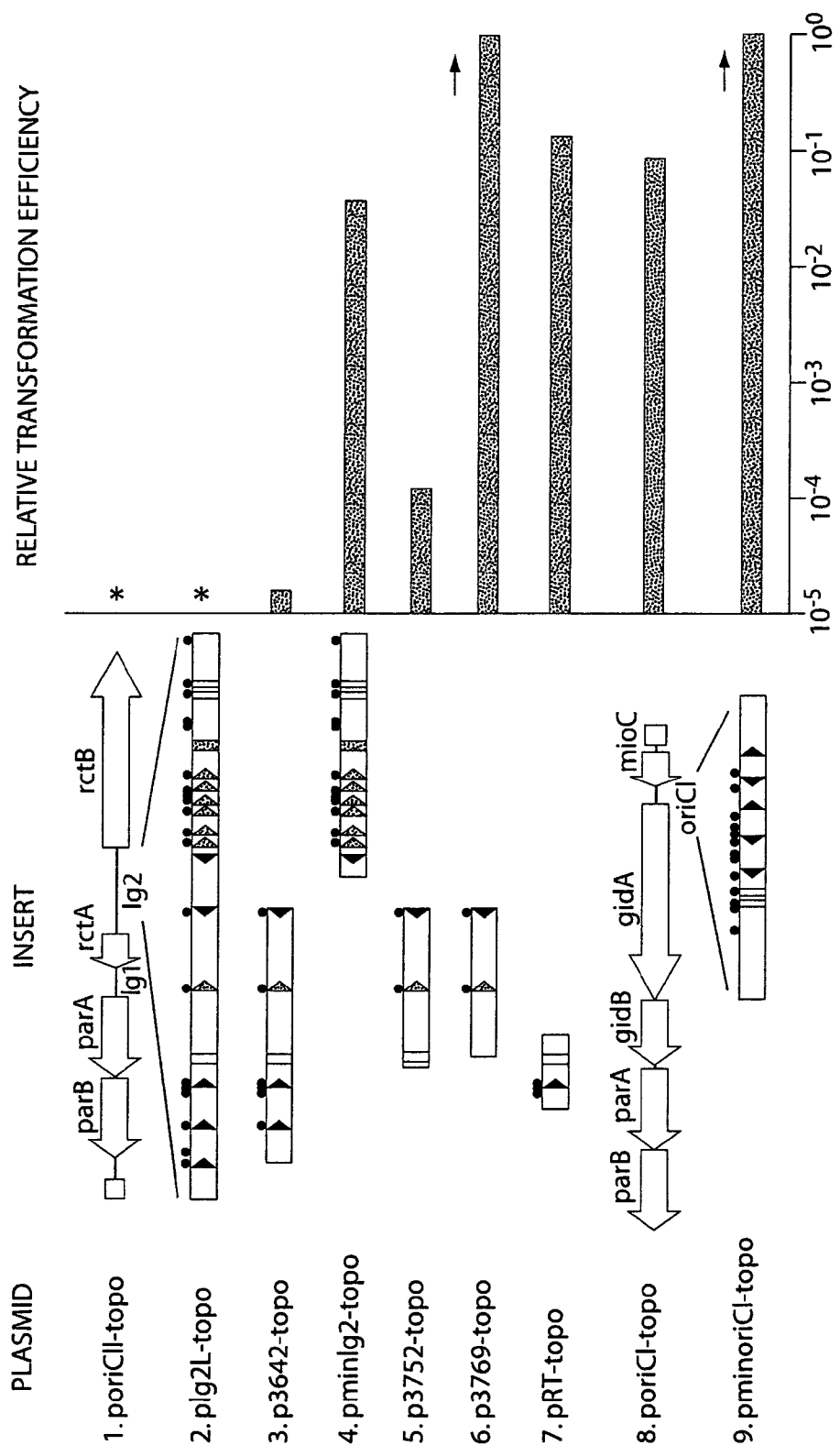
FIG. 4 is a drawing and a bar graph showing that a *V. cholerae* incompatibility determinant maps to the left side of ig2. DNA segments from the oriCII$_{vc}$ and oriCI$_{vc}$ regions were cloned into the high-copy vector pCRII-TOPO (obtained from Invitrogen Corp., Carlsbad, Calif.). The features of the oriCII$_{vc}$ and oriCI$_{vc}$ regions are annotated as in FIG. 2 except for a highly conserved 13 bp sequence (shown in FIG. 8). Each plasmid (100 ng) was used to transform electrocompetent *V. cholerae* N 16961, and transformants were obtained on selective media. The relative transformation efficiency was calculated as the number of transformants obtained for each plasmid compared to the number obtained with vector alone. The results shown are those of one representative experiment of at least two done for each plasmid. The asterisks in lines 1 and 2 indicate that the number of transformants was below assay detection (<3× 10$^{-6}$). The arrows in lines 6 and 9 indicate that the relative transformation efficiency was slightly greater than 1.0.

The presence of a chrII incompatibility sequence was confirmed by transforming *V. cholerae* with a high copy number vector containing chrII or chrI sequences and measuring the transformation efficiency compared to vector alone. When high-copy poriCII-topo, pIg2L-topo, or a 407 bp segment from the left side of ig2 (p3642-topo) were introduced into *V. cholerae*, the transformation efficiency was more than 90,000-fold lower than the efficiency of transforming vector alone (FIG. 4, lines 1–3). In contrast, high-copy pmInIg2 (pmInIg2-topo) transformed *V. cholerae* almost as efficiently as vector alone (FIG. 4, line 4), confirming that an incompatibility determinant (inc) is contained within the left side of ig2. Additional mapping experiments revealed that incompatibility depends on a short highly conserved sequence present in *V. cholerae*, *V. vulnificus*, *V. harveyi*, *V. parahaemolyticus*, and *V. fischeri* (FIG. 4, lines 5–6; Supplemental FIG. S2). While this conserved region clearly contributes to incompatibility, it is not the sole determinant, because a smaller insert (in pRT-topo) that included the conserved segment transformed *V. cholerae* efficiently (FIG. 4, line 7).

Unlike chrII minichromosomes and high-copy oriCII$_{vc}$ sequences, plasmids containing oriCI$_{vc}$ sequences were not incompatible with *V. cholerae*. High copy number plasmids containing either a 5.2 kb region encompassing oriCI$_{vc}$ (poriCI-topo) or the minimal oriCI$_{vc}$ (pminoriCI-topo) were readily introduced into *V. cholerae* and did not compromise viability (FIG. 4, lines 8–9). In this regard, oriCI$_{vc}$ is similar to *E. coli* oriC, which in relatively high copy is not toxic in *E. coli*.

Figure 5:
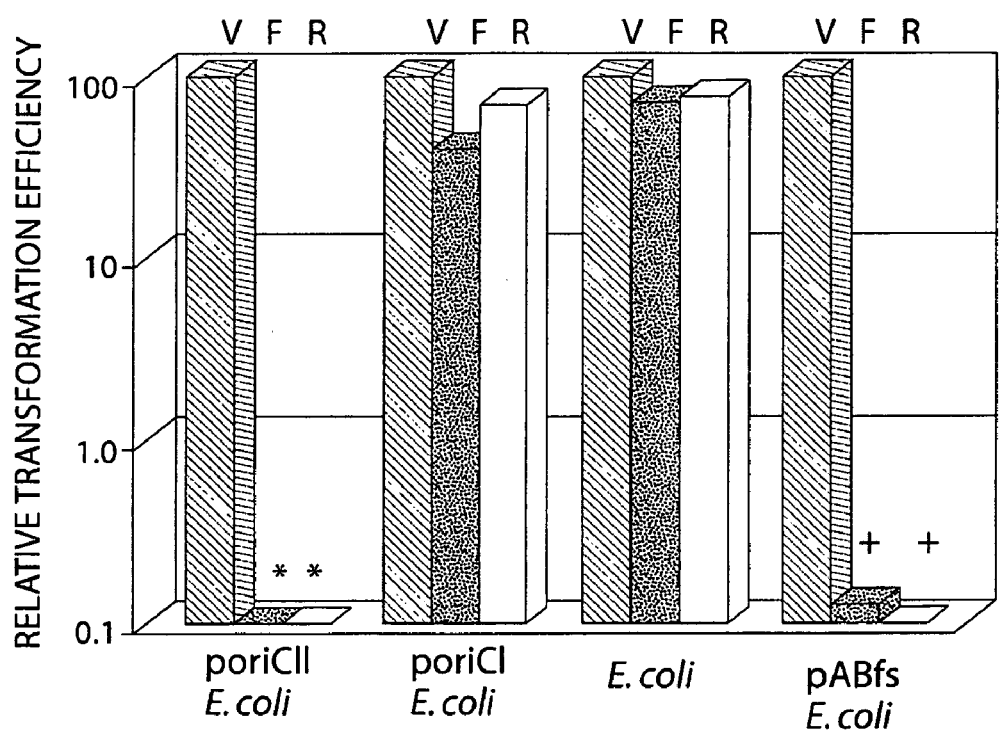
FIG. 5 is a bar graph showing that the ig2 incompatibility determinant influences the replication region of poriCII but not poriCI. The ColD plasmid pGZ119 (V) or derivatives containing the 407 bp insert from plasmid p3642-topo (see FIG. 4) in either the forward (F) (plasmid pEE481) or reverse (R) (plasmid pEE482) orientation were used to transform the recA *E. coli* strain KB1. Where indicated, the *E. coli* strain harbored another plasmid: poriCII, pABfs (poriCII with frameshift mutations in parA and parB), or poriCI. Transformants were selected on LB-agar containing ampicillin (for the resident plasmid) and chloramphenicol (for the transforming plasmid). The relative transformation efficiency was calculated by dividing the number of transformants obtained for each plasmid by the number of transformants obtained with vector alone within each strain. The asterisks and crosses indicate that the relative transformation efficiency for these data points, respectively, was below detection by this assay (<0.007 and <0.13, respectively). The results shown are means of at least two experiments.

To test whether sequence from the left side of ig2 (termed inc) specifically interfered with the replication regions of one or both *V. cholerae* chromosomes, *E. coli* containing either poriCII or poriCI was used so that the *V. cholerae* minimal replicons could be studied in relative isolation. The transformation of poriCII-containing *E. coli* by a vector containing the inc region (pEE481 or pEE482) was >10,000-fold lower than by vector alone (FIG. 5). The orientation of inc in the vector did not alter this effect (FIG. 5). When these plasmids were introduced into either poriCI-containing *E. coli* or *E. coli* without a minichromosome, there was virtually no difference in the transformation efficiency between vector alone and vector with insert (FIG. 5). Thus, inc renders a vector incompatible with poriCII but not poriCI; these findings are consistent with a role for inc in control of chrII but not chrI replication and/or partitioning.

To begin to define the mechanism of incompatibility, frameshift mutations in the putative poriCII were created in the partitioning genes parA and parB. The resulting plasmid, pABfs, was still incompatible with pEE481 and pEE482 in *E. coli* (FIG. 5), suggesting that incompatibility is not due to interactions of the left side of ig2 with these putative partitioning proteins. Instead, incompatibility appears to result from an influence of the inc region on the chrII replication machinery. Since pABfs contains both rctA and rctB and depends on them for replication, we hypothesize that the incompatibility region negatively regulates chrII replication by interacting with RctA and/or RctB.

Example 6

Minichromosomes Derived from the *V. cholerae* Chromosomes are dnaA-Dependent

Replication of many bacterial chromosomes and some plasmids is mediated by DnaA, which binds to the ori and stimulates strand unwinding to initiate replication (Hansen et al. 1986 and Messer et al. 1996). DnaA proved essential for replication of minichromosomes derived from both *V. cholerae* chromosomes, as neither of these plasmids could replicate in a dnaA-independent *E. coli* strain (Table 2). Thus, dnaA differs from rctB and rctA, which are only required for chromosome II replication. Since the activity of DnaA is regulated in a cell cycle-dependent fashion (Kurokawa et al. 1999), this protein may help coordinate replication of the two chromosomes.

TABLE 2

DnaA Is Required for Replication of poriCII and pminoriCI

| Plasmid[1] | Frequency of Exconjugant Formation[2] | |
|---|---|---|
| | *E. coli* dnaA⁺ pir[3] | *E. coli* dnaA pir[4] |
| poriCII | $1.1 \times 10^{-1}$ | $9.4 \times 10^{-6}$ |
| pminoriCI | $7.0 \times 10^{-2}$ | $<2.3 \times 10^{-6}$ |
| CloDF13 | $1.0 \times 10^{-1}$ | $5.0 \times 10^{-2}$ |

Example 7

DNA Adenine Methyltransferase (dam) is Required for *V. cholerae* Replication

Figure 6A:
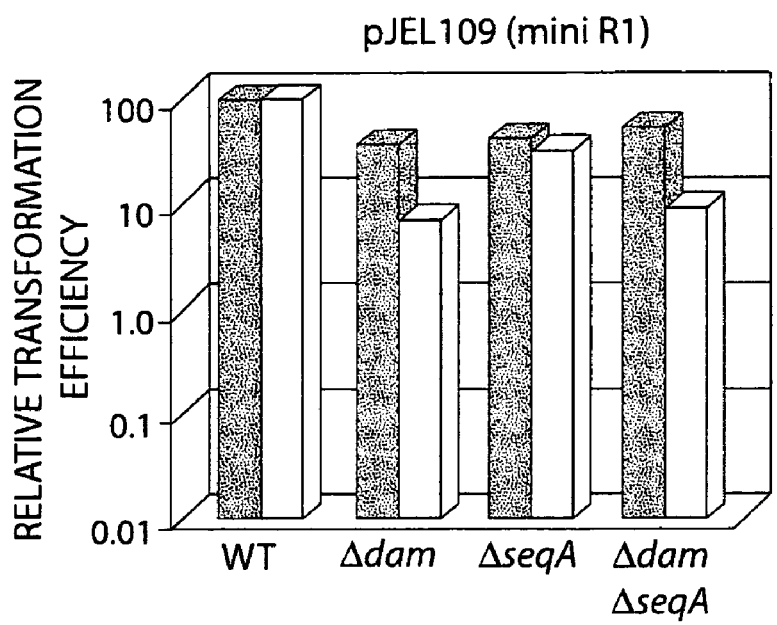
FIGS. 6A–6D are bar graphs showing that replication of poriCII and poriCI requires dam, and poriCI replication also requires seqA. A transformation-based assay was used to assess the replication capacity of four constructs. To calculate relative transformation efficiency, the number of transformants isolated from each of the four strain backgrounds was divided by the number isolated from the wild type (wt) strain and expressed as a percent. This calculation was performed separately for methylated (black or solid bars) and unmethylated (white or open bars) versions of each plasmid. Each transformation was done at least twice, and the relative transformation efficiencies were calculated using the averages from these experiments.
Figure 6B:
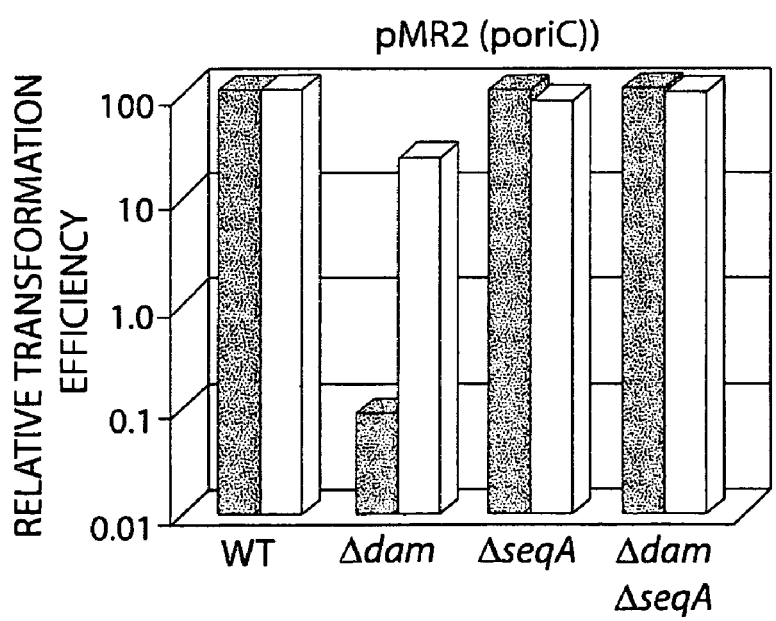

The roles of dam and DNA methylation in replication of the two *V. cholerae* minichromosomes were compared to its role in replication of an oriC minichromosome, since Dam methylation sites are overrepresented within all three sequences (see FIG. 2A). In *E. coli*, dam is not essential for oriC replication, but Dam methylation regulates the timing of replication initiation at oriC (Boye et al. 2000 and Marinus 1996). As has been observed in several previous studies (e.g., Lu et al. 1994 and Russell et al. 1987), a methylated *E. coli* oriC minichromosome was found to transform dam *E. coli* ~1000-fold less efficiently than wt *E. coli* (FIG. 6B). This reduction has been attributed to the binding and sequestration of hemimethylated oriC DNA by the SeqA protein to prevent reinitiation (Campbell et al., 1990 and Lu et al. 1994). When methylated poriC is used to transform dam *E. coli*, it is replicated once and then becomes hemimethylated and sequestered. Replication cannot be reinitiated because there is no Dam methylase in the cell. Consistent with this mechanism, dam *E. coli* can be transformed almost as efficiently as wt *E. coli* when unmethylated DNA is used (FIG. 6B). Similarly, methylated poriC is able to transform a dam seqA double mutant because SeqA-mediated sequestration of oriC no longer occurs (Lu et al., 1994) (FIG. 6B).

Figure 6C:
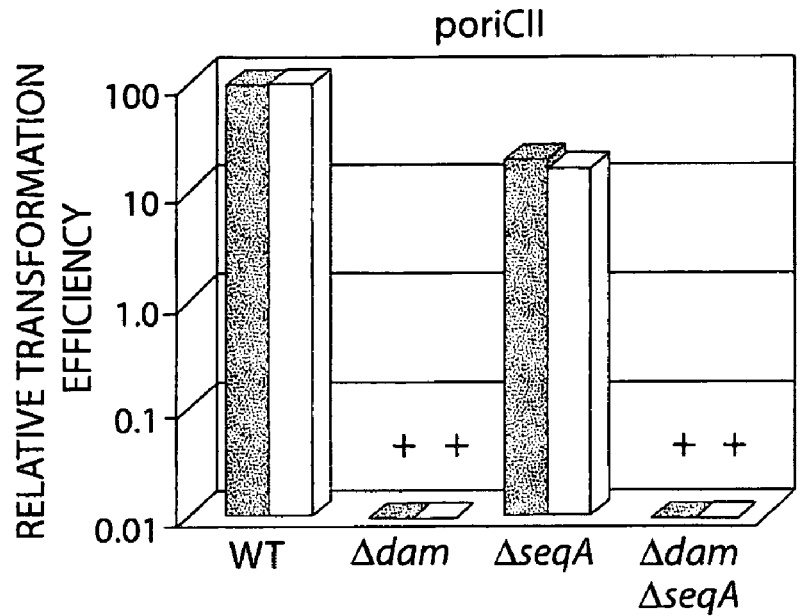

Dam plays a different role in replication of the *V. cholerae* minichromosomes than it does for poriC. Transformation of dam *E. coli* by methylated poriCII was ~10,000-fold less frequent than transformation of isogenic wt *E. coli*. Unlike poriC, unmethylated poriCII did not transform dam *E. coli*, suggesting that replication of poriCII absolutely requires Dam methylation (FIG. 6C). Consistent with this idea, poriCII did not transform a dam seqA double mutant (FIG. 6C). This indicates that methylation of oriCII$_{vc}$ contributes directly to its replication rather than or in addition to simply being a target for sequestration.

Figure 6D:
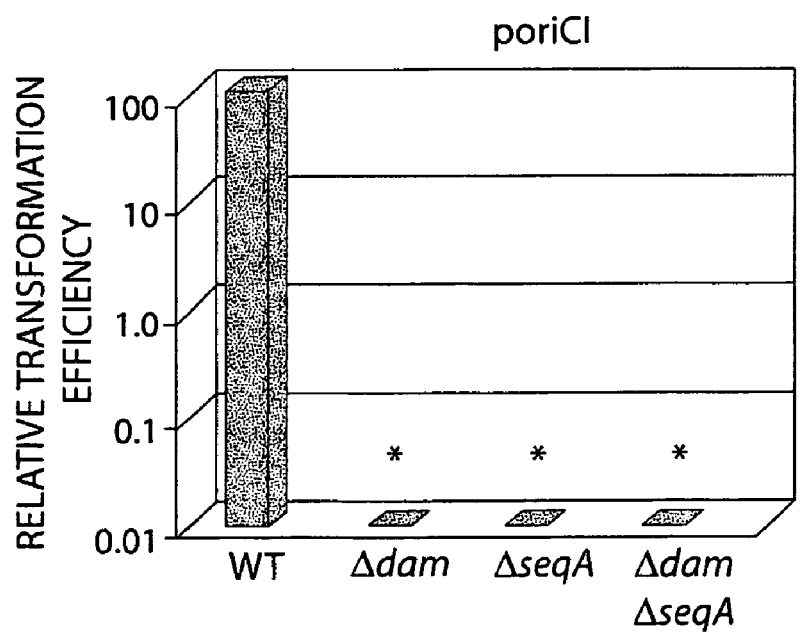

Dam methylation is required for poriCI replication as well, since dam *E. coli* could not be transformed with methylated poriCI (FIG. 6D). Surprisingly, seqA *E. coli* could not be transformed with poriCI, suggesting that seqA is required for replication of poriCI (FIG. 6D). Attempts to knock out *V. cholerae* seqA (54% identity and 69% similarity to *E. coli* SeqA) were unsuccessful, indicating that seqA is an essential gene in *V. cholerae*. In *E. coli*, several activities of SeqA contribute to control of replication. In addition to its role in binding and sequestering hemimethylated origin DNA, SeqA has been shown to influence transcriptional regulation, DNA superhelicity, and nucleoid structure (Slominska et al. 2001 and Weitao et al. 2000). The data herein indicate that in *V. cholerae*, seqA plays distinct roles in replication of chrI and chrII. Given the different effects of a seqA mutation on replication of poriCI and poriC, the roles of seqA in *V. cholerae* may prove to be different from those described in *E. coli*.

Example 8

Sequences

The sequences below were obtained and entered into the public database, GenBank Accession No.: NC_002506.

RctB nucleic acid (nucleotides 1134-3110 of NC_002506) is SEQ ID NO: 1 as used herein and in the claims has the following nucleotide sequence:

```
atgagctcagaagaaaaacgattgatcaaattgccaagaactcacaaagatggtcatcttttttgaagtctctgaagccgcgattgac    (SEQ ID NO: 1)

tggattgaacagtatcaacactttaaaggtgtcacgaaaagcattgttgaacttttgaatctgatctcactgcgtggattacgcagt agagatggcttagtttcaaccacagaactgattgatgcaaccgatgggcagctgacgcgtgcagccatccagcagcgcttgagagca gcggtagctgttggattgttcaaacaaatcccagtgcgttttgaagaggggctggctggcaaaaccatgctccatcgtttcattaac cccaaccaattgatctcggtactcggctcaaccagcttagtcactgaatcggttaagcaaaatgaaaagcaaaagcgctcaaaagca ttagcgcagacgcaagtcaatcaacgtactgcatgagcatggtttaaatacaccgccagccatgaaagatgaggctgatcagtttgt ggtctcaccgactaactgggcagggatcattgatcaagcgttagcgccacccagaacccgcaagagctaccaaaagtctatggtttc gatatcgggtactcgtgctgtgattgaaacacgatcgtctaaaaacatcatgacggtcgacgatctgatgactttgtttgccttatt cactttaacagtgcaataccatgatcatcaccaagatgattaccatttcaatgctaaacaagcaccaaacaaaacgccgctgtatat caccgacattctctctttacgtggcaaaaaagacagcggcccggcacgtgactcgatccgtgacagtattgatcgtattgaatttac cgattttcagttgcatgaactgacgggtcgttggctcagtgagaatatgccagaaggctttaaaagcgatcgtttcgcttttagc gcgcaccatcaccgcttccgaagaggcacctgtggaaggcagtgatggcgagatccgcatcaaacccaatctgtacattttggtgtg ggagccttcgttttttgaagagctattgacgcgagattatttcttcctatttccaccggagatcttgaaacaacataccttggtatt tcagctctactcctatttccgtagccgaatgtctcgtcgtcataccgatgtaatgatgctgagtgaactcaaccaaaaattggccag aaacatcgaatggcgacggttttctatggatctgatccgcgaacttcgtcgtctctccgaagggaagggagtgaagatctgtttgt ggtcaatctctgggttatcacttgactgtgaaaagcattgaagagaaaggcaaagtggtggattaccaagtcgatatcaaatgtga tgtggaagaggtactgcgctattcacgcgccaaaaccaccaacgcgggtaaacgcaatatggctccaaccttgcctaacccctttacg taacgagctggtttccaagcagaaactggctgagttatcgagcatcatcgatggtgaatttgaaccaatccagcgcaaagcccttc gccgagaggccgcttaggtcggcgcgtgaagctacgtaaacatcttgtcgaaatcaatgctgatgaaatcaccattactctatcgcg ttatacctctccagaagcgctagaacgcagtataacggctttagcggctatgactggacacgcccttcatcaatcaagaagagtg tgtagagctcatagacaagctagattggctgcgtgttgaaaacgatgtgatccaatacccgacttgagcaagctgcttgagctctac aacagccaaaatgagagtaaacatctgtcgatcgaaaaattgatcgcaggtttagcggtacgccgtaaagtctgtaaattggttcaa gatgggcacattgacgaaacggtgtatcgagccttagatgagatggccgctggagcctaa
```

RctB gene product (658 amino acids) as used herein and in the claims is SEQ ID NO: 2, and has the following amino acid sequence:

(SEQ ID NO: 2)
MSSEEKRLIKLPRTHKDGHLFEVSEAAIDWIEQYQHFKGVTKSIVELLNL

ISLRGLRSRDGLVSTTELIDATDGQLTRAAIQQRLRAAVAVGLFKQIPVR

FEEGLAGKTMLHRFINPNQLISVLGSTSLVTESVKQNEKQKRSKALAQTQ

VNQRLLHEHGLNTPPAMKDEADQFVVSPTNWAGIIDQALAPPRTRKSYQK

SMVSISGTRAVIETRSSKNIMTVDDLMTLFALFTLTVQYHDHHQDDYHFN

AKQAPNKTPLYITDILSLRGKKDSGPARDSIRDSIDRIEFTDFQLHELTG

RWLSENMPEGFKSDRFRFLARTITASEEAPVEGSDGEIRIKPNLYILVWE

PSFFEELLTRDYFFLFPPEILKQHTLVFQLYSYFRSRMSRRHTDVMMLSE

LNQKLARNIEWRRFSMDLLRELRRLSEGKGSEDLFVVNLWGYHLTVKSIE

EKGKVVDYQVDIKCDVEEVLRYSRAKTTNAGKRNMAPTLPNPLRNELVSK

QKLAELSSIIDGEFEPIQRKAPSPRGRLGRRVKLRKHLVEINADEITITL

SRYTSPEALERSITALAAMTGHAPSSIKEECVELIDKLDWLRVENDVIQY

PTLSKLLELYNSQNESKHLSIEKLIAGLAVRRKVCKLVQDGHIDETVYRA

LDEMAAGA

RctA (nucleotides 112-246 of NC_002506) as used herein and in the claims is SEQ ID NO: 3, and has the following nucleotide sequence:

(SEQ ID NO: 3)
tcacttatttacaatgtaaagccacgttttgaagtgatgatgaataaata aaagcgagccgtaagcggaacgattaaaccgagccactaagttacggtga atgccattctgattgaaatgatgcgcaggattcaa Discussion The Origins of Replication of *V. cholerae* chrI and chrII The basic features of *E. coli* oriC have, until now, been thought to define chromosomal origins of replication in γ-proteobacteria (Messer and Weigel 1996 and Zyskind et al. 1983). Examples herein show that while oriCI$_{vc}$ largely conforms to this pattern, i.e., oriCII$_{vc}$ shares certain features with oriC, including a DnaA box, several sites for Dam methylation, and an AT-rich region, this origin also has several unusual features for a bacterial chromosome. Unlike other known chromosomes, oriCII$_{vc}$-based replication was determined to require, in addition to DnaA, a novel DNA binding protein, a repeat sequence, and an RNA; furthermore, a noncoding sequence negatively regulates chrII replication.

Our assertion that oriCII$_{vc}$ represents the true origin of replication of chrII is supported by a genetic screen for origins of replication in *V. harveyi* (Zyskind et al., 1983). This study led to the isolation of an autonomously replicating sequence that we show herein contains a sequence similar to oriCII$_{vc}$. Furthermore, the oriCII$_{vc}$ region is conserved among at least three other *Vibrio* species, and rctB was found in many diverse members of the family Vibrionaceae, so that these are general among this family.

An RNA is Required for poriCII Replication

Several examples indicate that the rctA gene product is an RNA and not a protein. First, neither of two different single base pair changes within rctA affected replication of poriCII even though both of these mutations introduced stop codons into the predicted rctA open reading frame (ORF), one of which was at the start codon (FIG. 1B, lines 11–12). Second, rctA is not conserved among related *Vibrio* species. A lack of conservation at the DNA sequence level might be expected for a functional RNA, which could retain conservation at the structural level. Finally, new algorithms for ORF identification that account for codon usage suggest that there is no protein-coding gene in the area of rctA (Guo et al., 2003). An RNA that spans the annotated vca0001 gene was detected by RPA analysis, but the precise boundaries and function of the RctA RNA are not known. transacting RNA molecules have been described in plasmid replication (del Solar et al., 1998), and in *E. coli*, transcriptional activity at oriC is believed to influence replication efficiency (Messer and Weigel, 1996). RctA RNA may function directly in replication (e.g., as a primer) or may play a required regulatory role.

A Negative Regulator of chrII Replication

An incompatibility determinant that was localized to a DNA sequence adjacent to the minimal oriCII$_{vc}$ region was found to negatively influence oriCII$_{vc}$-but not oriCI$_{vc}$-based replication. Plasmid replication is often controlled by negative regulators (del Solar et al., 1998), which maintain copy number within a narrow range to avoid overtaxing the host. Plasmid inc regions can negatively regulate replication by titration of essential replication factors (either protein or RNA) (del Solar et al. 1998 and Novick 1987) or by "handcuffing," in which Rep proteins bound to the ori sterically hinder replication initiation (Chattoraj, 2000). Data herein, without being limited by any particular theory or mechanism, are consistent with either regulatory mechanisms controlling oriCII$_{vc}$-based replication, presumably by influencing of these availability of RctA and/or RctB or by RctB-mediated handcuffing of oriCII$_{vc}$. If this is the case, replication of chrII may at least in part be controlled independently of chrI.

Is oriCII$_{vc}$ Plasmid-Like?

OriCII$_{vc}$-based replication has four features that characterize certain plasmid replicons: a repeat sequence essential for replication, a dependence on a replicon-specific protein (RctB), a requirement for an RNA (RctA), and an incompatibility determinant (inc) that appears to act as a negative regulator. Therefore that chrII may originally have been acquired as a plasmid and subsequently captured essential genes (Heidelberg et al. 2000). Since we found that the *V. cholerae* replication protein-encoding gene rctB is present in many genera of the family Vibrionaceae, the hypothetical plasmid ancestor of chrII must have been acquired prior to diversification of this family.

Some of the plasmid-like attributes of oriCII$_{vc}$-based replication are different from those of characterized plasmids, and the four novel features have never been described together in a single replicon. The origins of replication of iteron-type plasmids are characterized by the presence of short repeated sequences (iterons) to which a plasmid-encoded replication protein (Rep) binds (del Solar et al., 1998). Rep binding to iterons in the ori stimulates strand unwinding, and Rep-iteron interactions, both within the ori and in nearby control regions, are involved in controlling copy number through handcuffing (Chattoraj, 2000). While RctB may be classified as a Rep protein and the 11-mer and 12-mer sequences in oriCII$_{vc}$ as iterons however, data herein suggest that these repeats do not function as typical plasmid iterons. Though the 12-mers are required for oriCII$_{vc}$-based replication, in gel shift assays a single 12-mer was not bound by RctB. Furthermore, RctB bound to probes containing no apparent repeat sequences (FIG. 2B, iii). The 11- and 12-mer repeats in oriCII$_{vc}$ also do not appear to function as iterons in replication control. In the iteron plasmid P1, a single iteron can exert incompatibility because it is bound by Rep and can therefore facilitate handcuffing (Papp et al., 1994). In contrast, in *V. cholerae* a sequence with six 12-mer repeats was not sufficient to exert incompatibility (FIG. 4, line 4). Even if RctB functions analogously to a plasmid Rep protein, it is important to note that RctB has no sequence similarity to known plasmid Rep proteins and has no recognizable motifs.

Control of Replication in a Bacterium with Two Chromosomes

How of a bacterium with multiple chromosomes, to ensure that each daughter cell. At least three general scenarios regarding replication, receives a full genome complement at cell division, can be envisioned: (1) each chromosome replicates using the same factors, (2) the chromosomes have entirely distinct replication requirements, or (3) the chromosomes share some common factors yet also maintain some distinct requirements. Analysis of the two *V. cholerae* chromosomes herein revealed that replication of each chromosome involved specific factors (rctB, rctA, and a control region for chrII and seqA for chrI), and that the chromosomes also shared a requirement for certain factors (dnaA and dam). Having some common and some distinct factors may be biologically favorable in a multichromosomal bacterium because this mechanism could allow for some degree of coordinated replication while minimizing competition among the replicons.

Since the two *Vibrio* chromosomes appear to have coexisted throughout Vibrionaceae speciation, we presume that there is coordination of their replication (unlike the unlinked replication of plasmids and their hosts' chromosomes (del Solar et al., 1998). Without being bound by any particular mechanism of action, the factors shared by both chromosomes, including DnaA and Dam methylation, may mediate this coordination. *V. cholerae* DnaA is very similar to that of *E. coli* (79% aa identity), and *E. coli* DnaA can enable both oriCI$_{vc}$- and oriCII$_{vc}$-based replication, suggesting that *V. cholerae* DnaA may function and be regulated as in *E. coli*. Sharing this essential and highly regulated (Katayama et al. 1998 and Kitagawa et al. 1996) initiation factor could ensure that replication of each chromosome is initiated only during a small time window in each cell cycle.

The other major shared factor identified, herein, Dam methyltransferase, may be essential for replication of both *V. cholerae* chromosomes. This observation may explain why dam is an essential gene in *V. cholerae* (Julio et al., 2001). Aside from its role in regulation of replication in *E. coli*, dam to influences DNA structure in some origins of replication, such as the P1 plasmid ori (Abeles et al. 1993). However, the requirement for dam in *V. cholerae* may differ from that P1, in because unmethylated P1-derived plasmids can transform dam *E. coli* (Abeles et al. 1993). Dam may play several roles in *V. cholerae* chromosome replication. As in *E. coli*, it may remethylate DNA that has been sequestered by SeqA due to hemimethylation. However, it is clear that dam must also play additional roles, since poriCII could not replicate in a dam host even in the absence of seqA. The methylation state of oriCII$_{vc}$ could affect binding of replication factors including RctB or RctA. Alternatively, oriCI$_{vc}$ and oriCII$_{vc}$ structures may be influenced by methylation in a manner similar to the ori of P1; providing a means by which the two *V. cholerae* origins are activated by methylation in a cell-cycle dependent and potentially synchronous manner.

Since the sequences of oriCI$_{vc}$ and oriC are similar, it is surprising that dam appeared essential for oriCI$_{vc}$-based replication (FIG. 6D). It is possible that poriCI competes with the *E. coli* host chromosome for the available initiator molecules in the absence of Dam methylation. Such competition is believed to result in integration of oriC minichromosomes into the chromosome of dam *E. coli* (Lobner-Olesen and von Freiesleben 1996); in the absence of sufficient sequence homology for poriCI integration, competing poriCI plasmids may not be maintained in dam *E. coli*. If poriCI does compete with oriC in the absence of Dam methylation, then dam must regulate oriCI$_{vc}$-based replication. The importance of dam in both oriCII$_{vc}$- and oriCI$_{vc}$-based replication is consistent with a role for Dam methylation in coordination of replication of the two *V. cholerae* chromosomes.

A bipartite genomic arrangement has persisted throughout Vibrionaceae speciation. Since there are many duplicated loci present on both *V. cholerae* chromosomes, it is surprising that the two chromosomes have remained separate replicons throughout evolution. Division of the genome into two chromosomes may provide an evolutionary advantage either by facilitating a faster replication time or by allowing for chromosome-specific replication control in certain environmental circumstances. This evolutionary advantage might be eclipsed by competition between two replicons with identical replication initiation factors. The distinct replication requirements of chrI and chrII may minimize competition and thereby help ensure the maintenance of the divided genome.

REFERENCES

Abeles, A., et al., 1993. Evidence of two levels of control of P1 oriR and host oriC replication origins by DNA adenine methylation. *J. Bacteriol.* 175, pp. 7801–7807.

Boye, E. et al., 1990. The role of dam methyltransferase in the control of DNA replication in *E. coli. Cell* 62, pp. 981–989.

Boye, E., et al., 2000. Limiting DNA replication to once and only once. *EMBO Rep.* 1, pp. 479–483.

Bramhill, D. et al., 1988. Duplex opening by dnaA protein at novel sequences in initiation of replication at the origin of the *E. coli* chromosome. *Cell* 52, pp. 743–755.

Cabezon, E., et al., 1997. Genetic evidence of a coupling role for the TraG protein family in bacterial conjugation. *Mol. Gen. Genet.* 254, pp. 400–406.

Campbell, J. et al., 1990. *E. coli* oriC and the dnaA gene promoter are sequestered from dam methyltransferase following the passage of the chromosomal replication fork. *Cell* 62, pp. 967–979.

Chattoraj, D. K., 2000. Control of plasmid DNA replication by iterons: no longer paradoxical. *Mol. Microbiol.* 37, pp. 467–476.

del Solar, et al., 1998. Replication and control of circular bacterial plasmids. *Microbiol. Mol. Biol. Rev.* 62, pp. 434–464.

DelVecchio, et al. et al., 2002. The genome sequence of the facultative intracellular pathogen *Brucella melitensis. Proc. Natl. Acad. Sci. USA* 99, pp. 443–448.

Fuller, R. S., et al., 1984. The DnaA protein complex with the *E. coli* chromosomal replication origin (oriC) and other DNA sites. *Cell* 38, pp. 889–900.

Guo, F. B., et al., 2003. Zcurve: a new system for recognizing protein-coding genes in bacterial and archaeal genomes. *Nucleic Acids Res.* 31, pp. 1780–1789.

Hansen, E. B. et al., 1986. Host participation in plasmid maintenance: dependence upon dnaA of replicons derived from P1 and F. *Proc. Natl. Acad. Sci. USA* 83, pp. 4423–4427.

Heidelberg, et al., 2000. DNA sequence of both chromosomes of the cholera pathogen *Vibrio cholerae*. *Nature* 406, pp. 477–483.

Jensen, et al., 1990. *Escherichia coli* minichromosomes: random segregation and absence of copy number control. *J. Mol. Biol.* 215, pp. 257–265.

Julio, S. M., et al., 2001. DNA adenine methylase is essential for viability and plays a role in the pathogenesis of *Yersinia pseudotuberculosis* and *Vibrio cholerae*. *Infect. Immun.* 69, pp. 7610–7615.

Katayama, et al., 1998. The initiator function of DnaA protein is negatively regulated by the sliding clamp of the *E. coli* chromosomal replicase. *Cell* 94, pp. 61–71.

Kitagawa, R., et al., 1996. A novel DnaA protein-binding site at 94.7 min on the *Escherichia coli* chromosome. *Mol. Microbiol.* 19, pp. 1137–1147.

Kita-Tsukamoto, et al., 1993. Phylogenetic relationships of marine bacteria, mainly members of the family Vibrionaceae, determined on the basis of 16S rRNA sequences. *Int. J. Syst. Bacteriol.* 43, pp. 8–19.

Kurokawa, K., et al., 1999. Replication cycle-coordinated change of the adenine nucleotide-bound forms of DnaA protein in *Escherichia coli*. *EMBO J.* 18, pp. 6642–6652.

Lessl, M., et al., 1992. Dissection of IncP conjugative plasmid transfer: definition of the transfer region Tra2 by mobilization of the Tra1 region in trans. *J. Bacteriol.* 174, pp. 2493–2500.

Lobner-Olesen, A. et al., 1996. Chromosomal replication incompatibility in Dam methyltransferase deficient *Escherichia coli* cells. *EMBO J.* 15, pp. 5999–6008.

Lobner-Olesen, A., et al., 1992. Expression of the *Escherichia coli* dam gene. *Mol. Microbiol.* 6, pp. 1841–1851.

Lu, M., et al., 1994. SeqA: a negative modulator of replication initiation in *E. coli*. *Cell* 77, pp. 413–426.

Marinus, M. G., 1996. Methylation of DNA. In: Neidhardt, F. C., Editor, 1996. *Escherichia coli and Salmonella*, ASM Press, Washington, D.C. 782–791 pp.

Marszalek, J. et al., 1994. DnaA protein directs the binding of DnaB protein in initiation of DNA replication in *Escherichia coli*. *J. Biol. Chem.* 269, pp. 4883–4890.

Messer, W. et al., 1996. Initiation of chromosome replication. In: Neidhardt, F. C., Editor, 1996. *Escherichia coli and Salmonella*, ASM Press, Washington, D.C. 1579–1601 pp.

Miller, V. L. et al, J. J., 1988. A novel suicide vector and its use in construction of insertion mutations: osmoregulation of outer membrane proteins and virulence determinants in *Vibrio cholerae* requires *toxR*. *J. Bacteriol.* 170, pp. 2575–2583.

Moyer, K. E., et al., 2001. Evidence for a rolling-circle mechanism of phage DNA synthesis from both replicative and integrated forms of CTXϕ. *Mol. Microbiol.* 41, pp. 311–323.

Novick, R. P., 1987. Plasmid incompatibility. *Microbiol Rev.* 51, pp. 381–395.

Papp, P. P., et al., 1994. Negative control of plasmid DNA replication by iterons. Correlation with initiator binding affinity. *J. Biol. Chem.* 269, pp. 23563–23568.

Pearson, G. D., et al., 1993. CTX genetic element encodes a site-specific recombination system and an intestinal colonization factor. *Proc. Natl. Acad. Sci. USA* 90, pp. 3750–3754.

Russell, D. W. et al., 1987. Hemimethylation prevents DNA replication in *E. coli*. *Cell* 50, pp. 1071–1079.

Slominska, M., et al., 2001. SeqA, the *Escherichia coli* origin sequestration protein, is also a specific transcription factor. *Mol. Microbiol.* 40, pp. 1371–1379.

Trucksis, M., et al., 1998. The *Vibrio cholerae* genome contains two unique circular chromosomes. *Proc. Natl. Acad. Sci. USA* 95, pp. 14464–14469.

Weitao, et al., 2000. *Escherichia coli* cell cycle control genes affect chromosome superhelicity. *EMBO Rep.* 1, pp. 494–499.

Yamaichi, Y., et al., 1999. Physical and genetic map of the genome of *Vibrio parahaemolyticus*: presence of two chromosomes in *Vibrio* species. *Mol. Microbiol.* 31, pp. 1513–1521.

Zyskind, J. W., et al., 1983. Chromosomal replication origin from the marine bacterium *Vibrio harveyi* functions in *Escherichia coli*: oriC consensus sequence. *Proc. Natl. Acad. Sci. USA* 80, pp. 1164–1168.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, issued patents, and published patent applications cited throughout this application are hereby incorporated by reference. The appropriate components, processes, and methods of those patents, applications and other documents may be selected for the present invention and embodiments thereof.

We claim:

1. A method of screening for an antibacterial agent capable of inhibiting chromosomal nucleic acid replication in cells of a bacterial species of the family of Vibrionaceae, said method comprising:
   contacting a test cell with a candidate agent;
   measuring replication of the nucleic acid in the test cell and in a control cell not contacted with the candidate agent; and
   comparing replication of the nucleic acid in the test cell with replication of nucleic acid in the control cell,
   whereby a decrease in replication of the nucleic acid in the test cell relative to the replication of nucleic acid in the control cell, is the absence of the candidate and otherwise identical, identifies the candidate agent as an antibacterial agent capable of inhibiting nucleic acid replication in the cell.

2. The method according to claim 1, wherein measuring replication is further analyzing by a method selected from the group of measuring: cell growth; specific activity of a cell enzyme; DNA incorporation of a radiolabel; and cell content of a gene on chromosome II of the cell.

3. The method according to claim 1, wherein the species is selected from the group of genera consisting of: *Aeromonas, Allomonas, Beneckea, Enhydrobacter, Listonella, Lucibacterium, Photobacterium, Plesimonas, Salinivibrio*, and *Vibrio*.

4. The method according to claim 3, wherein the bacterial cell is a pathogen.

5. The method according to claim 1, wherein the agent is bacteriostatic.

6. The method according to claim 1, wherein the agent is bactericidal.

* * * * *